(12) United States Patent
Daigle

(10) Patent No.: US 10,136,645 B2
(45) Date of Patent: Nov. 27, 2018

(54) ANTIMICROBIAL COMPOSITION

(71) Applicant: MicroBio Solutions Inc., Canton de Hatley (CA)

(72) Inventor: Francois Daigle, Canton de Hatley (CA)

( * ) Notice: Subject to any disclaimer, the term of this patent is extended or adjusted under 35 U.S.C. 154(b) by 6 days.

(21) Appl. No.: 15/546,073

(22) PCT Filed: Feb. 5, 2016

(86) PCT No.: PCT/CA2016/050106
§ 371 (c)(1),
(2) Date: Jul. 25, 2017

(87) PCT Pub. No.: WO2016/123716
PCT Pub. Date: Aug. 11, 2016

(65) Prior Publication Data
US 2018/0007909 A1 Jan. 11, 2018

Related U.S. Application Data

(60) Provisional application No. 62/113,014, filed on Feb. 6, 2015.

(51) Int. Cl.
| | | |
|---|---|---|
| *A01N 47/42* | (2006.01) |
| *A61K 47/12* | (2006.01) |
| *A61K 9/08* | (2006.01) |
| *A61K 9/00* | (2006.01) |
| *A01N 59/00* | (2006.01) |
| *A61K 31/223* | (2006.01) |
| *A23B 4/24* | (2006.01) |
| *A01N 25/22* | (2006.01) |
| *A01N 47/44* | (2006.01) |
| *A23B 4/20* | (2006.01) |
| *A61L 2/18* | (2006.01) |
| *A23L 3/358* | (2006.01) |
| *A23B 7/154* | (2006.01) |
| *A23B 7/157* | (2006.01) |
| *A61K 33/40* | (2006.01) |
| *A23L 3/3526* | (2006.01) |

(52) U.S. Cl.
CPC ............ *A01N 47/42* (2013.01); *A01N 25/22* (2013.01); *A01N 47/44* (2013.01); *A01N 59/00* (2013.01); *A23B 4/20* (2013.01); *A23B 4/24* (2013.01); *A23B 7/154* (2013.01); *A23B 7/157* (2013.01); *A23L 3/358* (2013.01); *A23L 3/3526* (2013.01); *A61K 9/0014* (2013.01); *A61K 9/08* (2013.01); *A61K 31/223* (2013.01); *A61K 33/40* (2013.01); *A61K 47/12* (2013.01); *A61L 2/18* (2013.01)

(58) Field of Classification Search
None
See application file for complete search history.

(56) References Cited

U.S. PATENT DOCUMENTS

2006/0040847 A1 2/2006 Weibel

FOREIGN PATENT DOCUMENTS

| CA | 2867879 | 10/2013 | |
|---|---|---|---|
| WO | WO2001/65939 | 9/2001 | |
| WO | WO2011/119517 | 9/2011 | |
| WO | WO 2016/028265 A1 * | 2/2016 | ............... A61K 8/44 |

OTHER PUBLICATIONS

International Search Report dated Apr. 22, 2016 from the corresponding patent application PCT/CA2016/050106.

* cited by examiner

*Primary Examiner* — Brian J Davis
(74) *Attorney, Agent, or Firm* — Benoit & Cote Inc.; Mathieu Miron

(57) ABSTRACT

The present application describes an antimicrobial composition comprising lauric arginate ethyl ester (LAE) and hydrogen peroxide and the use of this composition for disinfecting and sanitizing different types of surfaces such as food products, human skin or mucosa and hard surfaces as well as a method of stabilizing the composition by including a sequestering agent (citrate salt and/or phosphate salt).

27 Claims, No Drawings

ANTIMICROBIAL COMPOSITION

CROSS-REFERENCE TO RELATED APPLICATIONS

This application is a US National Phase application under 35 USC § 371 of PCT/CA2016/050106, filed Feb. 5, 2016, which claims priority from and the benefit of U.S. Provisional Application No. 62/113,014, filed Feb. 6, 2015, the specifications of which are hereby incorporated by reference in their entireties.

BACKGROUND

(a) Field

The subject matter disclosed generally relates to antimicrobial compositions, and specifically, to antimicrobial compositions that are useful at disinfecting and sanitizing different type of surface including food products, human skin or mucosa, and hard surfaces. The compositions of the present invention include a mixture of lauric arginate ethyl ester (LAE) with hydrogen peroxide. The compositions of the present invention comprise natural, GRAS, food grade or food additive raw materials.

(b) Related Prior Art

The field of the invention relates to the prevention of infections, including food security and the prevention of nosocomial infections. Pathogens such as bacteria, fungi, viruses, and bacterial spores are responsible for infection of human, as well as contamination of food, biological samples and environments. These pathogens can be found present on the surface of meats, fruits, vegetables or any others hard and porous surfaces. The first step in microbial infections is generally the direct or indirect contact with pathogens by ingestion, inhalation, or skin or mucous membrane contact, followed by subsequent invasion and dissemination of the infectious microbe. The portals of entry of pathogenic bacteria are predominantly the skin and mucus membranes.

In a concept of food safety, a contamination can occur at any time, from the culture or breeding of the food, during the processing, to preparation and packaging of food products. Thus the food product may encounter microorganisms which may make it unsuitable for consumption. The microorganisms may come from the food itself, the food contact surfaces, and/or the surrounding environment. The microorganisms can range from pathogenic microorganisms (e.g., *Listeria monocytogenes*, enterohemorrhagic *Escherichia coli, Salmonella* and the like) to spoilage organisms that can affect the taste, color, and/or smell of the final food product (e.g., *Pseudomonas, Acinetobacter, Moraxella, Alcaligenes, Flavobacterium, Erwinia*, and the likes). Microorganisms can affect a wide variety of food products, including meat, poultry, fish and shellfish, cheese, fruits and vegetables, and pre-prepared foods. At certain levels, the presence of microorganisms on a food product may cause everything from a consumer's perception of a lower quality product, to regulatory investigations and sanctions, to foodborne illness and death.

Reducing the occurrence of the foodborne pathogen in foods is an important food safety goal, particularly due to the relatively high infection levels and even mortality, associated with some pathogens.

Food processors use a variety of methods during processing to control and/or reduce the presence of microorganisms on food products. These methods include everything from cleaning and sanitizing the food processing plant environment, applying or incorporating antimicrobials to or in the food product, irradiating the food product, applying heat, and other pasteurization or sterilization techniques. Applying or incorporating an antimicrobial composition to or in the food product is a common way of controlling microorganisms. However, it is difficult to formulate a composition that is effective at reducing microorganisms using ingredients that are acceptable for direct food contact according to government regulations. Further, it is difficult to formulate a composition that can be applied directly to a food product without adversely affecting the color, taste, or smell of the food product. Finally, once a food product has been treated with an antimicrobial composition or process to control the presence of microorganisms on the food product, the opportunity exists for the food product to become re-contaminated during further processing.

In the food industry, an important aspect that must be considered now in the control of microorganisms and preservation of food is that consumers increasingly demand foods which retain their natural flavour, colour and texture and contain fewer additives such as preservatives. In response to these needs, one of the most important recent developments in the food industry has been the development of minimal processing technologies designed to limit the impact of processing on nutritional and sensory quality and to preserve food without the use of synthetic additives. Therefore, it has become important to formulate antimicrobial solutions and preservations agent used in a food process with a minimum of quality ingredients.

Therefore, there exists a need in the art for antimicrobial compositions that provide a hospital grade activity spectrum disinfectant and which may have ability to act as a food grade preservative or sanitizer and be applied directly to the foods before their consumptions due to its negligible toxicity.

SUMMARY

According to an embodiment, there is provided an antimicrobial composition comprising:
a) Lauric arginate ethyl ester; and
b) hydrogen peroxide.

The antimicrobial composition may further comprise a carrier.

The antimicrobial composition may further comprise a sequestering agent.

The concentration said of lauric arginate ethyl ester is from about 0.001% to about 5% w/w.

The concentration of said lauric arginate ethyl ester is from about 0.01% to about 2.5% w/w.

The concentration of said lauric arginate ethyl ester is from about 0.01% to about 0.1% w/w.

The concentration of lauric arginate ethyl ester is of at least about 5 ppm.

The hydrogen peroxide may be obtained from a solid peroxide salts.

The hydrogen peroxide salt may be selected from the group consisting of sodium percarbonate, calcium peroxide, hydrogen peroxide-urea (i.e. carbamide peroxide), and combinations thereof.

The concentration of said hydrogen peroxide is from about 0.001% to about 35% w/w.

The concentration of said hydrogen peroxide is from about 0.01% to about 20% w/w.

The concentration of said hydrogen peroxide is from about 0.05% to about 15% w/w.

The concentration of hydrogen peroxide is of at least about 5 ppm.

The lauric arginate ethyl ester and said hydrogen peroxide are in a weight ratio of about 1:200 to about 10:1.

The lauric arginate ethyl ester and said hydrogen peroxide are in a weight ratio of about 1:100 to about 5:1.

The lauric arginate ethyl ester and said hydrogen peroxide are in a weight ratio of about 1:40 to about 2:1.

The lauric arginate ethyl ester and said hydrogen peroxide are in a weight ratio of about 1:5 to about 1:1.

The lauric arginate ethyl ester and said hydrogen peroxide are in a weight ratio of about 1:40, or 1:10, or 1:2, or 5:1.

The sequestering agent may be selected from the group consisting of citric acid, phosphoric acid or their salt, and mixtures thereof.

The sequestering agent is composed of natural, GRAS or food additive raw materials.

The concentration of said sequestering agent may be from about 0.0001 to about 2% w/w of the composition.

The composition may further comprise a stabilizing agent.

The concentration of said stabilizing agent may be from about 0.015% to about 0.5% w/w of the composition.

The composition may further comprise one or more additional antimicrobial ingredient.

The additional antimicrobial ingredient may be selected from a group consisting of organic acid, essentials oils, chitosan, bacteriocin and combinations thereof.

The organic acid may be selected from the group consisting of lactic acid, acetic acid, propionic acid, citric acid, sodium citrate, disodium pyrophosphate, potassium phosphate, sodium phosphate, phosphoric acid, and combinations thereof.

The composition may further comprise an additional ingredient selected from the group consisting of an oxidizer, a hydrotrope, a thickening agent, a gelling agent, a foaming agent, a foaming inhibitor, a film-forming agent, a surfactant, a coupling agent, a acidulant, a potentiator, a corrosion inhibitor, an anti-browning agent, an antioxidant, a systemic acquired resistance inducer, a long chain fatty acid, a flavouring agent, a fragrance, a dye, and mixtures thereof.

The essential oil comprises oils of anise, lemon oil, orange oil, oregano oil, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, *eucalyptus* oil, tea tree oil, vervain oil, peppermint oil, gum benzoin, basil oil, fennel oil, fir oil, balsam oil, menthol, ocmea *origanum* oil, Hydastis carradensis oil, Berberidaceae daceae oil, Ratanhiae and *Curcuma longa* oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, ylang ylang, or combinations thereof.

The acidulant may be selected from lactic acid, phosphoric acid, sulfuric acid, adipic acid, tartaric acid, succinic acid, acetic acid, propionic acid, citric acid, malic acid, sodium acid sulfate, octenyl succinic acid, octanoic acid, glucolic acid, levulinic acid and mixtures thereof.

The concentration of said acidulant may be from about 0.0001% to about 1% w/w of the composition.

The buffer may be selected from sodium citrate, potassium citrate, sodium phosphate, disodium pyrophosphate, or combinations thereof.

The concentration of said buffer may be from about 0.001% to about 5% w/w of the composition.

The long chain fatty acid may be selected from hexanoic (C6) acid, octanoic (C8) acid, nonanoic (C9) acid, decanoic (O10) acid, lauric (C12) acid, myristic (C14) acid, palmitic (C16) acid, stearic (C18) acid, arachidic (C20) acid, behenic (C22) acid, palmitoleic (C16:1) acid, oleic (C18:1) acid, linoleic (C18:2) acid, linolenic (C18:3) acid, arachidonic (C20:1) acid.

The concentration of said long chain fatty acids from about 0.0001% to about 5% w/w of the composition.

The oxidizer may be selected from benzoyl peroxide, tert-butyl benzoyl peroxide, performic acid, peracetic acid, perlactic acid, perglycolic acid, chloroperbenzoic acid, perheptanoic acid, peroctanoic acid, perdecanoic acid, percitric acid, perbenzoic acid, adipic acid, succinic acid, glutaric acid, sebacic acid, or malonic acid, oxygen, ozone, chlorine dioxide, and combinations thereof.

The concentration of said oxidizer may be from about 0.001 to about 70% w/w of said composition.

The carrier may be selected from water, a solvent, or combinations thereof or a solid carrier.

The solvent may be selected from an alcohol, a polyol, or combinations thereof.

The alcohol may be selected from methanol, ethanol, propanol, and isopropanol.

The polyol may be a C2-C6 polyol.

The polyol may be selected from propylene glycol, ethylene glycol, glycerine, and 1,2-propanediol.

The carrier may be present in a quantity sufficient to reach 100% w/w.

The thickening agent may be selected from xanthan gum, tragacanth gum, karaya gum, acacia gum; carageenan, locust bean gum, guar gum, pectin, carboxymethyl cellulose, methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, carboxymethylcellulose, polyvinylpyrrolidone, polyvinylmethylether, polyacrylic acid, polymethacrylic acid, polyacrylamide, polyethylene oxide, and polyethyleneimine or combinations thereof.

The concentration of said thickening agent and/or a gelling agent may be about 0.001 to about 20% w/w of said composition.

The foaming agent may be selected from an alcohol ethoxylate, an alcohol ethoxylate carboxylate, an amine oxide, an alkyl sulfate, an alkyl ether sulfate, a sulfonate, a quaternary ammonium compound, an alkyl sarcosine, a betaine, and an alkyl amide.

The concentration of said foaming agent may be from about 0.001 to about 20% w/w of said composition.

The film-forming agent may be selected from colloidal aluminum silicate, colloidal magnesium aluminum silicate, colloidal clays, polyvinyl pyrrolidone, polyvinyl acetate, polyvinyl alcohol, polyalkylene oxides, polyacrylamides, chitosan, a silica, and mixtures thereof.

The concentration of said film-forming agent may be from about 0.01 to about 50% w/w of said composition.

The surfactant may be selected from include nonionic surfactants, anionic surfactants, cationic surfactants, amphoteric surfactants, amine oxides, or combinations thereof.

The surfactant may be linoleic acid, a sorbitan ester, a sugar ester, a lecithin, an ethoxylated lecithin, a PEG alkylate, an linear alkylbenzene sulfonate, a stearyl citrate, an alkyl naphthalene sulfonate, a pluronic acid, or combinations thereof.

The concentration of said surfactant may be from about 0.001 to about 20% w/w of said composition.

The potentiator may be selected from α-terpinene, cineole, citral, citronellal, citronellol, farnesol, geraniol, limonene, linalool, methone, nerolidol, terpineol, camphene, menthone, myrcene, nerol, tetrahydrogeraniol, tetrahydrolinalool, apritone, and bisabolol, or combinations thereof.

The concentration of said potentiator may be from about 0.001 to about 1% w/w.

The corrosion inhibitor may be 1-hydroxyethylidene-1,1-diphosphonic acid.

The antibrowning agent or antioxidant may be selected from ascorbic acid or derivatives or isomers thereof, citric acid, malic acid, fumaric acid, lactic acid, succinic acid, pyruvic acid, oxalacetic acid, quinic acid, tartaric acid, alginic acid, pectinic acid, ethylenediaminetetraacetic acid (EDTA), sodium acid pyrophosphate, 4-hexylresorcinol, chitosan, calcium carbonate, calcium sulphate, calcium chloride, calcium phosphate, calcium tartrate, an antioxidant enzyme, and mixtures thereof.

The systemic acquired resistance inducer may be selected from of a silicate salt, acibenzolar-5-methyl, amino-n-butyric acid, aminobenzoic acid, riboflavin, salicylic acid, or combinations thereof.

The concentration of said systemic acquired resistance inducer may be from about 0.001 to about 10% w/w of said composition.

The composition may have a pH from about 2.0 to about 7.0.

The composition may be for use for the disinfection of a surface.

The composition may be for use for the prevention of bacterial growth.

The composition may be for use as a fungicide.

The composition may be for use for the prevention of a bacterial spore.

According to another embodiment, there may be provided a method of disinfecting a surface comprising contacting to said surface with a composition according to the present invention.

The surface may comprise the surface of fruit or vegetables.

The surface may comprise the surface of a meat product, an animal carcass, a live poultry, a live animal, human skin, or a plant.

The surface may comprise the surface of a food processing equipment, a hard surface, a porous surface, a medical equipment, a surface in a health care facility.

The composition may be used as a concentrate composition.

The composition may be used as a diluted composition.

According to another embodiment, there is provided a method for stabilizing a composition comprising lauric arginate ethyl and hydrogen peroxide, and prevent reduction of said hydrogen peroxide, comprising including a sequestering agents selected from the group consisting of a citrate salt, a phosphate salt, and mixtures thereof in said composition.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

The term "hard water" as used herein refers to water having a high concentration of dissolved minerals and solids.

The term "GRAS" as used herein refers to generally recognized as safe (GRAS), is an American Food and Drug Administration (FDA) designation that a chemical or substance added to food considered safe by experts, and so is exempted from the usual Federal Food, Drug, and Cosmetic Act (FFDCA) food additive tolerance requirements.

The use of the terms "antimicrobial" in this application does not mean that any resulting products are approved for use as an antimicrobial agent.

The term "packaged food product" is intended to mean a food product that has been placed in packaging but not yet sealed.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing the compounds of the present invention and an acceptable, a pharmaceutically acceptable or non-pharmaceutically acceptable carrier(s). By "pharmaceutically acceptable" or "acceptable" it is meant the carrier, diluent or excipient must be compatible with the other ingredients of the formulation and not deleterious to the recipient thereof.

In some embodiments, the term "pharmaceutically acceptable" or "acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier. Saline solutions and aqueous dextrose and glycerol solutions can also be employed as liquid carriers, particularly for injectable solutions. Suitable pharmaceutical excipients or non-pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders and the like. Such compositions will contain an effective amount of the LAE and hydrogen peroxide, preferably in purified form, together with a suitable amount of carrier so as to provide the form for proper administration to the patient. The formulation should suit the mode of administration.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

DETAILED DESCRIPTION

In embodiments there is disclosed an antimicrobial composition comprising lauric arginate ethyl ester and hydrogen peroxide.

The present invention relates to antimicrobial solutions comprising a combination of Lauric arginate ethyl ester (LAE) and hydrogen peroxide. By combining the LAE with hydrogen peroxide alone or in combination with other molecules of natural origin or recognized GRAS compounds (e.g. essential oil, bacteriocin, chitosan or organic acid), the antimicrobial effect of each of the LAE and hydrogen peroxide compound is synergistically enhanced, thereby reducing the amount of each active compound and therefore reduce the disadvantages of each compound, such as toxicity and the oxidation power. Furthermore, the use of multiple active molecules (two or more) that have different antimicrobial action mechanism greatly reduces the risk that microorganisms develop resistance mechanisms.

The composition of the present invention has a high antimicrobial efficacy which is useful in the prevention of surface contamination, including food surface. Specifically, the antimicrobial composition of the invention may be used in applications as a sanitizer or disinfectant to reduce or eliminate microbial pathogens on the surface of foods such as fruits, vegetables and meat. Moreover, the composition may be used in any number of other applications which require the applications of an antimicrobial composition that leaves a residue that is readily acceptable in terms of toxicity or appearance (non-contamination) for food or hygienic products, for human and animal skin, or for plant growth.

Surprisingly, the combination of hydrogen peroxide and the LAE, two molecules of food grade and US-FDA "GRAS" qualification, provides a synergistic antimicrobial activity, which results in increased speed of action and an improved spectrum of antimicrobial activity. It is also surprising to note that the stabilizers (e.g. acid and/or sequestering agent) used in the hydrogen peroxide to limited degradation, also stabilized the LAE in solutions by increasing the solubility and homogeneity of LAE in the solution while at a pH range which is optimal in for antimicrobial activity. The present invention allows reducing several problems caused by use of a high concentration of LAE powder in solution and high concentrations of hydrogen peroxide. Furthermore, synergy reduces the quantity of each active ingredient needed to obtain the same antimicrobial efficacy.

Ethyl Lauroyl Arginate

Ethyl lauroyl arginate is produced by esterification of arginine with ethanol, and subsequently reacting the ester with lauroyl chloride. The resultant ethyl lauroyl arginate is recovered as a hydrochloride salt. This is also referred to as lauric arginate ethyl ester, or simply lauric arginate, and is commonly referred to by the term LAE. In the human body, LAE is rapidly metabolized to the naturally occurring dietary components lauric acid and arginine. Thus, LAE has a low toxicity and high antimicrobial activity that makes it a suitable tool for controlling or preventing microbial growth on food products or as a contact antimicrobial. Lauric arginate ethyl ester (LAE) is commercially available as a water soluble powder, but most often as a concentrate solution at 10 to 20% of LAE, mainly mixed with propylene glycol, and also arginate, maltodextrine, ethanol or polysorbate for the solubilization and the stability of LAE in solution. Lauric arginate ethyl ester has been promoted as a food preservative. It has also been used to limited extent as a contact antimicrobial. However, the activity spectrum of LAE is limited when the contact time is short and the use of a single cationic surfactant promotes the development of microorganisms resistance against the antimicrobial. Furthermore, the concentrate solution forms available commercially are very costly, which limits their use as a contact antimicrobial for most applications.

The widespread utilization of LAE within the food industry or as an antimicrobial solution may be limited for a number of reasons. LAE is a cationic surfactant that can interact strongly with either anionic or hydrophobic groups on other molecules, which may have important consequences for its practical application. Interactions with other components of antimicrobial products may alter its solubility and therefore affect the stability of final antimicrobial products in aqueous solutions. For example, in mildly acidic conditions, LAE exists in aqueous solutions as a small micelles which, according to its concentration, does not strongly scatter light and thus compromises the transparency of the system, and will cause aggregates formation or precipitate over the time. In addition, the antimicrobial activity of LAE may be adversely affected if it interacts with other components within a complex system, since this will change its charge and ability to interact with bacterial cell membranes. Finally, LAE is known to bind to anionic biopolymers naturally present within the mouth (e.g., mucins), which can lead to a perceived bitterness or astringency.

The concentration of LAE use in a disinfecting or sanitizing solution may be limited by the solubility of the molecule, by a possible respiratory irritation during use and also by the food industry regulatory standards which exists in different countries and limits the use above a certain concentration in product when an indirect or direct contact with food is possible.

The antimicrobial action of LAE is attributed to membrane disruption, where the compound disrupts the lipid bilayer in the bacterial membrane, and subsequent disturbance of vital cellular functions (e.g., potassium flux) and inhibiting cellular proliferation over a wide pH range (3-7). Because LAE is surface active and positively charged, it damages the cell membrane by reacting with negatively charged proteins or enzymes, thus causing their denaturation. This leads either to an inhibition of bacteria growth or cell death. In addition, LAE has a low oil-water equilibrium partition coefficient (KOW<0.1), which means it tends to concentrate in the water phase of products, where most bacterial activity occurs. The LAE leaves a slight residue on the surface that gives it a residual antimicrobial activity over time.

The antimicrobial activity of LAE, especially as a contact antimicrobial, presents some limitations in the spectrum of activity. For example, LAE has i) a reduced activity against Gram (−) microbes compared to the Gram (+) microbes, ii) no sporicidal activity, iii) poor activity against *pseudomonas*, iv) not effective against all nosocomial infections, v) lack tuberculocidal properties, vi) poor activity against hydrophilic viruses, and vii) may lead to the development of resistant bacterial strains when used alone.

LAE is one of the most potent food antimicrobial agents, with a broad spectrum of antimicrobial activity, and it has been classified as GRAS (Generally Recognized as Safe) and food preservative by the Food and Drug Administration (FDA) and also and also approved as a food preservative by the European Food Safety Authority (EFSA). LAE is use as an antimicrobial in more than 20 foods, including meat and poultry products. LAE is hydrolyzed in the human body and is metabolized rapidly to naturally occurring amino acids, mainly arginine and ornithine, after consumption, which is ultimately broken down into $CO_2$ and urea. LAE has been verified to be non-toxic, several toxicological studies were carried out with animals and human by the Huntingdon Life Science although these studies did not involve YOPIs (young, old, pregnant and immune-compromised). Also, animal toxicological studies showed that LAE has low acute toxicity, with systemic No Observable Adverse Effect Levels (NOAEL) established at 15,000 mg/L.

In embodiments, the compositions of the present invention may comprise from about 0.001 to about 5% w/w LAE, or from about 0.002 to about 5%, or from about 0.003 to about 5%, or from about 0.004 to about 5%, or from about 0.005 to about 5%, or from about 0.006 to about 5%, or from about 0.007 to about 5%, or from about 0.008 to about 5%, or from about 0.009 to about 5%, or from about 0.010 to about 5%, or from about 0.011 to about 5%, or from about 0.012 to about 5%, or from about 0.011 to about 5%, or from about 0.012 to about 5%, or from about 0.013 to about 5%, or from about 0.014 to about 5%, or from about 0.015 to about 5%, or from about 0.016 to about 5%, or from about 0.017 to about 5%, or from about 0.018 to about 5%, or from about 0.019 to about 5%, or from about 0.020 to about 5%, or from about 0.021 to about 5%, or from about 0.022 to about 5%, or from about 0.023 to about 5%, or from about 0.024 to about 5%, or from about 0.025 to about 5%, or from about 0.03 to about 5%, or from about 0.04 to about 5%, or from about 0.05 to about 5%, or from about 0.06 to about 5%, or from about 0.07 to about 5%, or from about 0.08 to about 5%, or from about 0.09 to about 5%, or from about 0.1 to about 5%, or from about 0.2 to about 5%, or from about 0.3 to about 5%, or from about 0.4 to about 5%, or from about 0.5 to about 5%, or from about 0.6 to about 5%, or from about 0.7 to about 5%, or from about 0.8 to about 5%, or from about 0.9 to about 5%, or from about 1 to about 5%, or from about 2 to about 5%, or from about 3 to about 5%, or from about 4 to about 5%, or from about 0.001 to about 4% w/w LAE, or from about 0.002 to about 4%, or from about 0.003 to about 4%, or from about 0.004 to about 4%, or from about 0.005 to about 4%, or from about 0.006 to about 4%, or from about 0.007 to about 4%, or from about 0.008 to about 4%, or from about 0.009 to about 4%, or from about 0.010 to about 4%, or from about 0.011 to about 4%, or from about 0.012 to about 4%, or from about 0.011 to about 4%, or from about 0.012 to about 4%, or from about 0.013 to about 4%, or from about 0.014 to about 4%, or from about 0.015 to about 4%, or from about 0.016 to about 4%, or from about 0.017 to about 4%, or from about 0.018 to about 4%, or from about 0.019 to about 4%, or from about 0.020 to about 4%, or from about 0.021 to about 4%, or from about 0.022 to about 4%, or from about 0.023 to about 4%, or from about 0.024 to about 4%, or from about 0.025 to about 4%, or from about 0.03 to about 4%, or from about 0.04 to about 4%, or from about 0.05 to about 4%, or from about 0.06 to about 4%, or from about 0.07 to about 4%, or from about 0.08 to about 4%, or from about 0.09 to about 4%, or from about 0.1 to about 4%, or from about 0.2 to about 4%, or from about 0.3 to about 4%, or from about 0.4 to about 4%, or from about 0.5 to about 4%, or from about 0.6 to about 4%, or from about 0.7 to about 4%, or from about 0.8 to about 4%, or from about 0.9 to about 4%, or from about 1 to about 4%, or from about 2 to about 4%, or from about 3 to about 4%, or from about 0.001 to about 3% w/w LAE, or from about 0.002 to about 3%, or from about 0.003 to about 3%, or from about 0.004 to about 3%, or from about 0.005 to about 3%, or from about 0.006 to about 3%, or from about 0.007 to about 3%, or from about 0.008 to about 3%, or from about 0.009 to about 3%, or from about 0.010 to about 3%, or from about 0.011 to about 3%, or from about 0.012 to about 3%, or from about 0.011 to about 3%, or from about 0.012 to about 3%, or from about 0.013 to about 3%, or from about 0.014 to about 3%, or from about 0.015 to about 3%, or from about 0.016 to about 3%, or from about 0.017 to about 3%, or from about 0.018 to about 3%, or from about 0.019 to about 3%, or from about 0.020 to about 3%, or from about 0.021 to about 3%, or from about 0.022 to about 3%, or from about 0.023 to about 3%, or from about 0.024 to about 3%, or from about 0.025 to about 3%, or from about 0.03 to about 3%, or from about 0.04 to about 3%, or from about 0.05 to about 3%, or from about 0.06 to about 3%, or from about 0.07 to about 3%, or from about 0.08 to about 3%, or from about 0.09 to about 3%, or from about 0.1 to about 3%, or from about 0.2 to about 3%, or from about 0.3 to about 3%, or from about 0.4 to about 3%, or from about 0.5 to about 3%, or from about 0.6 to about 3%, or from about 0.7 to about 3%, or from about 0.8 to about 3%, or from about 0.9 to about 3%, or from about 1 to about 3%, or from about 2 to about 3%, or from about 0.001 to about 2% w/w LAE, or from about 0.002 to about 2%, or from about 0.003 to about 2%, or from about 0.004 to about 2%, or from about 0.005 to about 2%, or from about 0.006 to about 2%, or from about 0.007 to about 2%, or from about 0.008 to about 2%, or from about 0.009 to about 2%, or from about 0.010 to about 2%, or from about 0.011 to about 2%, or from about 0.012 to about 2%, or from about 0.011 to about 2%, or from about 0.012 to about 2%, or from about 0.013 to about 2%, or from about 0.014 to about 2%, or from about 0.015 to about 2%, or from about 0.016 to about 2%, or from about 0.017 to about 2%, or from about 0.018 to about 2%, or from about 0.019 to about 2%, or from about 0.020 to about 2%, or from about 0.021 to about 2%, or from about 0.022 to about 2%, or from about 0.023 to about 2%, or from about 0.024 to about 2%, or from about 0.025 to about 2%, or from about 0.03 to about 2%, or from about 0.04 to about 2%, or from about 0.05 to about 2%, or from about 0.06 to about 2%, or from about 0.07 to about 2%, or from about 0.08 to about 2%, or from about 0.09 to about 2%, or from about 0.1 to about 2%, or from about 0.2 to about 2%, or from about 0.3 to about 2%, or from about 0.4 to about 2%, or from about 0.5 to about 2%, or from about 0.6 to about 2%, or from about 0.7 to about 2%, or from about 0.8 to about 2%, or from about 0.9 to about 2%, or from about 1 to about 2%, or from about 0.001 to about 1% w/w LAE, or from about 0.002 to about 1%, or from about 0.003 to about 1%, or from about 0.004 to about 1%, or from about 0.005 to about 1%, or from about 0.006 to about 1%, or from about 0.007 to about 1%, or from about 0.008 to about 1%, or from about 0.009 to about 1%, or from about 0.010 to about 1%, or from about 0.011 to about 1%, or from about 0.012 to about 1%, or from about 0.011 to about 1%, or from about 0.012 to about 1%, or from about 0.013 to about 1%, or from about 0.014 to about 1%, or from about 0.015 to about 1%, or from about 0.016 to about 1%, or from about 0.017 to about 1%, or from about 0.018 to about 1%, or from about 0.019 to about 1%, or from about 0.020 to about 1%, or from about 0.021 to about 1%, or from about 0.022 to about 1%, or from about 0.023 to about 1%, or from about 0.024 to about 1%, or from about 0.025 to about 1%, or from about 0.03 to about 1%, or from about 0.04 to about 1%, or from about 0.05 to about 1%, or from about 0.06 to about 1%, or from about 0.07 to about 1%, or from about 0.08 to about 1%, or from about 0.09 to about 1%, or from about 0.1 to about 1%, or from about 0.2 to about 1%, or from about 0.3 to about 1%, or from about 0.4 to about 1%, or from about 0.5 to about 1%, or from about 0.6 to about 1%, or from about 0.7 to about 1%, or from about 0.8 to about 1%, or from about 0.9 to about 1%, or from about 0.001 to about 0.9% w/w LAE, or from about 0.002 to about 0.9%, or from about 0.003 to about 0.9%, or from about 0.004 to about 0.9%, or from about 0.005 to about 0.9%, or from about 0.006 to about 0.9%, or from about 0.007 to about 0.9%, or from about 0.008 to about 0.9%, or from about 0.009 to about 0.9%, or from about 0.010 to about 0.9%, or from about 0.011 to about 0.9%, or from about 0.012 to about 0.9%, or from about 0.011 to about 0.9%, or from about 0.012 to about 0.9%, or from about 0.013 to about 0.9%, or from about 0.014 to about 0.9%, or from about 0.015 to about 0.9%, or from about 0.016 to about 0.9%, or from about 0.017 to about 0.9%, or from about 0.018 to about 0.9%, or from about 0.019 to about 0.9%, or from about 0.020 to about 0.9%, or from about 0.021 to about 0.9%, or from about 0.022 to about 0.9%, or from about 0.023 to about 0.9%, or from about 0.024 to about 0.9%, or from about 0.025 to about 0.9%, or from about 0.03 to about 0.9%, or from about 0.04 to about 0.9%, or from about 0.05 to about 0.9%, or from about 0.06 to about 0.9%, or from about 0.07 to about 0.9%, or from about 0.08 to about 0.9%, or from about 0.09 to about 0.9%, or from about 0.1 to about 0.9%, or from about 0.2 to about 0.9%, or from about 0.3 to about 0.9%, or from about 0.4 to about 0.9%, or from about 0.5 to about 0.9%, or from about 0.6 to about 0.9%, or from about 0.7 to about 0.9%, or from about 0.8 to about 0.9%, or from about 0.001 to about 0.8% w/w LAE, or from about 0.002 to about 0.8%, or from about 0.003 to about 0.8%, or from about 0.004 to about 0.8%, or from about 0.005 to about 0.8%, or from about 0.006 to about 0.8%, or from about 0.007 to about 0.8%, or from about 0.008 to about 0.8%, or from about 0.009 to about 0.8%, or from about 0.010 to about 0.8%, or from about 0.011 to about 0.8%, or from about 0.012 to about 0.8%, or from about 0.011 to about 0.8%, or from about 0.012 to about 0.8%, or from about 0.013 to about 0.8%, or from about 0.014 to about 0.8%, or from about 0.015 to about 0.8%, or from about 0.016 to about 0.8%, or from about 0.017 to about 0.8%, or from about 0.018 to about 0.8%, or from about 0.019 to about 0.8%, or from about 0.020 to about 0.8%, or from about 0.021 to about 0.8%, or from about 0.022 to about 0.8%, or from about 0.023 to about 0.8%, or from about 0.024 to about 0.8%, or from about 0.025 to about 0.8%, or from about 0.03 to about 0.8%, or from about 0.04 to about 0.8%, or from about 0.05 to about 0.8%, or from about 0.06 to about 0.8%, or from about 0.07 to about 0.8%, or from about 0.08 to about 0.8%, or from about 0.09 to about 0.8%, or from about 0.1 to about 0.8%, or from about 0.2 to about 0.8%, or from about 0.3 to about 0.8%, or from about 0.4 to about 0.8%, or from about 0.5 to about 0.8%, or from about 0.6 to about 0.8%, or from about 0.7 to about 0.8%, or from about 0.001 to about 0.7% w/w LAE, or from about 0.002 to about 0.7%, or from about 0.003 to about 0.7%, or from about 0.004 to about 0.7%, or from about 0.005 to about 0.7%, or from about 0.006 to about 0.7%, or from about 0.007 to about 0.7%, or from about 0.008 to about 0.7%, or from about 0.009 to about 0.7%, or from about 0.010 to about 0.7%, or from about 0.011 to about 0.7%, or from about 0.012 to about 0.7%, or from about 0.011 to about 0.7%, or from about 0.012 to about 0.7%, or from about 0.013 to about 0.7%, or from about 0.014 to about 0.7%, or from about 0.015 to about 0.7%, or from about 0.016 to about 0.7%, or from about 0.017 to about 0.7%, or from about 0.018 to about 0.7%, or from about 0.019 to about 0.7%, or from about 0.020 to about 0.7%, or from about 0.021 to about 0.7%, or from about 0.022 to about 0.7%, or from about 0.023 to about 0.7%, or from about 0.024 to about 0.7%, or from about 0.025 to about 0.7%, or from about 0.03 to about 0.7%, or from about 0.04 to about 0.7%, or from about 0.05 to about 0.7%, or from about 0.06 to about 0.7%, or from about 0.07 to about 0.7%, or from about 0.08 to about 0.7%, or from about 0.09 to about 0.7%, or from about 0.1 to about 0.7%, or from about 0.2 to about 0.7%, or from about 0.3 to about 0.7%, or from about 0.4 to about 0.7%, or from about 0.5 to about 0.7%, or from about 0.6 to about 0.7%, or from about 0.001 to about 0.6% w/w LAE, or from about 0.002 to about 0.6%, or from about 0.003 to about 0.6%, or from about 0.004 to about 0.6%, or from about 0.005 to about 0.6%, or from about 0.006 to about 0.6%, or from about 0.007 to about 0.6%, or from about 0.008 to about 0.6%, or from about 0.009 to about 0.6%, or from about 0.010 to about 0.6%, or from about 0.011 to about 0.6%, or from about 0.012 to about 0.6%, or from about 0.011 to about 0.6%, or from about 0.012 to about 0.6%, or from about 0.013 to about 0.6%, or from about 0.014 to about 0.6%, or from about 0.015 to about 0.6%, or from about 0.016 to about 0.6%, or from about 0.017 to about 0.6%, or from about 0.018 to about 0.6%, or from about 0.019 to about 0.6%, or from about 0.020 to about 0.6%, or from about 0.021 to about 0.6%, or from about 0.022 to about 0.6%, or from about 0.023 to about 0.6%, or from about 0.024 to about 0.6%, or from about 0.025 to about 0.6%, or from about 0.03 to about 0.6%, or from about 0.04 to about 0.6%, or from about 0.05 to about 0.6%, or from about 0.06 to about 0.6%, or from about 0.07 to about 0.6%, or from about 0.08 to about 0.6%, or from about 0.09 to about 0.6%, or from about 0.1 to about 0.6%, or from about 0.2 to about 0.6%, or from about 0.3 to about 0.6%, or from about 0.4 to about 0.6%, or from about 0.5 to about 0.6%, or from about 0.001 to about 0.5% w/w LAE, or from about 0.002 to about 0.5%, or from about 0.003 to about 0.5%, or from about 0.004 to about 0.5%, or from about 0.005 to about 0.5%, or from about 0.006 to about 0.5%, or from about 0.007 to about 0.5%, or from about 0.008 to about 0.5%, or from about 0.009 to about 0.5%, or from about 0.010 to about 0.5%, or from about 0.011 to about 0.5%, or from about 0.012 to about 0.5%, or from about 0.011 to about 0.5%, or from about 0.012 to about 0.5%, or from about 0.013 to about 0.5%, or from about 0.014 to about 0.5%, or from about 0.015 to about 0.5%, or from about 0.016 to about 0.5%, or from about 0.017 to about 0.5%, or from about 0.018 to about 0.5%, or from about 0.019 to about 0.5%, or from about 0.020 to about 0.5%, or from about 0.021 to about 0.5%, or from about 0.022 to about 0.5%, or from about 0.023 to about 0.5%, or from about 0.024 to about 0.5%, or from about 0.025 to about 0.5%, or from about 0.03 to about 0.5%, or from about 0.04 to about 0.5%, or from about 0.05 to about 0.5%, or from about 0.06 to about 0.5%, or from about 0.07 to about 0.5%, or from about 0.08 to about 0.5%, or from about 0.09 to about 0.5%, or from about 0.1 to about 0.5%, or from about 0.2 to about 0.5%, or from about 0.3 to about 0.5%, or from about 0.4 to about 0.5%, or from about 0.001 to about 0.4% w/w LAE, or from about 0.002 to about 0.4%, or from about 0.003 to about 0.4%, or from about 0.004 to about 0.4%, or from about 0.005 to about 0.4%, or from about 0.006 to about 0.4%, or from about 0.007 to about 0.4%, or from about 0.008 to about 0.4%, or from about 0.009 to about 0.4%, or from about 0.010 to about 0.4%, or from about 0.011 to about 0.4%, or from about 0.012 to about 0.4%, or from about 0.011 to about 0.4%, or from about 0.012 to about 0.4%, or from about 0.013 to about 0.4%, or from about 0.014 to about 0.4%, or from about 0.015 to about 0.4%, or from about 0.016 to about 0.4%, or from about 0.017 to about 0.4%, or from about 0.018 to about 0.4%, or from about 0.019 to about 0.4%, or from about 0.020 to about 0.4%, or from about 0.021 to about 0.4%, or from about 0.022 to about 0.4%, or from about 0.023 to about 0.4%, or from about 0.024 to about 0.4%, or from about 0.025 to about 0.4%, or from about 0.03 to about 0.4%, or from about 0.04 to about 0.4%, or from about 0.05 to about 0.4%, or from about 0.06 to about 0.4%, or from about 0.07 to about 0.4%, or from about 0.08 to about 0.4%, or from about 0.09 to about 0.4%, or from about 0.1 to about 0.4%, or from about 0.2 to about 0.4%, or from about 0.3 to about 0.4%, or from about 0.001 to about 0.3% w/w LAE, or from about 0.002 to about 0.3%, or from about 0.003 to about 0.3%, or from about 0.004 to about 0.3%, or from about 0.005 to about 0.3%, or from about 0.006 to about 0.3%, or from about 0.007 to about 0.3%, or from about 0.008 to about 0.3%, or from about 0.009 to about 0.3%, or from about 0.010 to about 0.3%, or from about 0.011 to about 0.3%, or from about 0.012 to about 0.3%, or from about 0.011 to about 0.3%, or from about 0.012 to about 0.3%, or from about 0.013 to about 0.3%, or from about 0.014 to about 0.3%, or from about 0.015 to about 0.3%, or from about 0.016 to about 0.3%, or from about 0.017 to about 0.3%, or from about 0.018 to about 0.3%, or from about 0.019 to about 0.3%, or from about 0.020 to about 0.3%, or from about 0.021 to about 0.3%, or from about 0.022 to about 0.3%, or from about 0.023 to about 0.3%, or from about 0.024 to about 0.3%, or from about 0.025 to about 0.3%, or from about 0.03 to about 0.3%, or from about 0.04 to about 0.3%, or from about 0.05 to about 0.3%, or from about 0.06 to about 0.3%, or from about 0.07 to about 0.3%, or from about 0.08 to about 0.3%, or from about 0.09 to about 0.3%, or from about 0.1 to about 0.3%, or from about 0.2 to about 0.3%, or from about 0.001 to about 0.2% w/w LAE, or from about 0.002 to about 0.2%, or from about 0.003 to about 0.2%, or from about 0.004 to about 0.2%, or from about 0.005 to about 0.2%, or from about 0.006 to about 0.2%, or from about 0.007 to about 0.2%, or from about 0.008 to about 0.2%, or from about 0.009 to about 0.2%, or from about 0.010 to about 0.2%, or from about 0.011 to about 0.2%, or from about 0.012 to about 0.2%, or from about 0.011 to about 0.2%, or from about 0.012 to about 0.2%, or from about 0.013 to about 0.2%, or from about 0.014 to about 0.2%, or from about 0.015 to about 0.2%, or from about 0.016 to about 0.2%, or from about 0.017 to about 0.2%, or from about 0.018 to about 0.2%, or from about 0.019 to about 0.2%, or from about 0.020 to about 0.2%, or from about 0.021 to about 0.2%, or from about 0.022 to about 0.2%, or from about 0.023 to about 0.2%, or from about 0.024 to about 0.2%, or from about 0.025 to about 0.2%, or from about 0.03 to about 0.2%, or from about 0.04 to about 0.2%, or from about 0.05 to about 0.2%, or from about 0.06 to about 0.2%, or from about 0.07 to about 0.2%, or from about 0.08 to about 0.2%, or from about 0.09 to about 0.2%, or from about 0.1 to about 0.2%, or from about 0.001 to about 0.1% w/w LAE, or from about 0.002 to about 0.1%, or from about 0.003 to about 0.1%, or from about 0.004 to about 0.1%, or from about 0.005 to about 0.1%, or from about 0.006 to about 0.1%, or from about 0.007 to about 0.1%, or from about 0.008 to about 0.1%, or from about 0.009 to about 0.1%, or from about 0.010 to about 0.1%, or from about 0.011 to about 0.1%, or from about 0.012 to about 0.1%, or from about 0.011 to about 0.1%, or from about 0.012 to about 0.1%, or from about 0.013 to about 0.1%, or from about 0.014 to about 0.1%, or from about 0.015 to about 0.1%, or from about 0.016 to about 0.1%, or from about 0.017 to about 0.1%, or from about 0.018 to about 0.1%, or from about 0.019 to about 0.1%, or from about 0.020 to about 0.1%, or from about 0.021 to about 0.1%, or from about 0.022 to about 0.1%, or from about 0.023 to about 0.1%, or from about 0.024 to about 0.1%, or from about 0.025 to about 0.1%, or from about 0.03 to about 0.1%, or from about 0.04 to about 0.1%, or from about 0.05 to about 0.1%, or from about 0.06 to about 0.1%, or from about 0.07 to about 0.1%, or from about 0.08 to about 0.1%, or from about 0.09 to about 0.1%, or from about 0.001 to about 0.09% w/w LAE, or from about 0.002 to about 0.09%, or from about 0.003 to about 0.09%, or from about 0.004 to about 0.09%, or from about 0.005 to about 0.09%, or from about 0.006 to about 0.09%, or from about 0.007 to about 0.09%, or from about 0.008 to about 0.09%, or from about 0.009 to about 0.09%, or from about 0.010 to about 0.09%, or from about 0.011 to about 0.09%, or from about 0.012 to about 0.09%, or from about 0.011 to about 0.09%, or from about 0.012 to about 0.09%, or from about 0.013 to about 0.09%, or from about 0.014 to about 0.09%, or from about 0.015 to about 0.09%, or from about 0.016 to about 0.09%, or from about 0.017 to about 0.09%, or from about 0.018 to about 0.09%, or from about 0.019 to about 0.09%, or from about 0.020 to about 0.09%, or from about 0.021 to about 0.09%, or from about 0.022 to about 0.09%, or from about 0.023 to about 0.09%, or from about 0.024 to about 0.09%, or from about 0.025 to about 0.09%, or from about 0.03 to about 0.09%, or from about 0.04 to about 0.09%, or from about 0.05 to about 0.09%, or from about 0.06 to about 0.09%, or from about 0.07 to about 0.09%, or from about 0.08 to about 0.09%, or from about 0.001 to about 0.08% w/w LAE, or from about 0.002 to about 0.08%, or from about 0.003 to about 0.08%, or from about 0.004 to about 0.08%, or from about 0.005 to about 0.08%, or from about 0.006 to about 0.08%, or from about 0.007 to about 0.08%, or from about 0.008 to about 0.08%, or from about 0.009 to about 0.08%, or from about 0.010 to about 0.08%, or from about 0.011 to about 0.08%, or from about 0.012 to about 0.08%, or from about 0.011 to about 0.08%, or from about 0.012 to about 0.08%, or from about 0.013 to about 0.08%, or from about 0.014 to about 0.08%, or from about 0.015 to about 0.08%, or from about 0.016 to about 0.08%, or from about 0.017 to about 0.08%, or from about 0.018 to about 0.08%, or from about 0.019 to about 0.08%, or from about 0.020 to about 0.08%, or from about 0.021 to about 0.08%, or from about 0.022 to about 0.08%, or from about 0.023 to about 0.08%, or from about 0.024 to about 0.08%, or from about 0.025 to about 0.08%, or from about 0.03 to about 0.08%, or from about 0.04 to about 0.08%, or from about 0.05 to about 0.08%, or from about 0.06 to about 0.08%, or from about 0.07 to about 0.08%, or from about 0.001 to about 0.07% w/w LAE, or from about 0.002 to about 0.07%, or from about 0.003 to about 0.07%, or from about 0.004 to about 0.07%, or from about 0.005 to about 0.07%, or from about 0.006 to about 0.07%, or from about 0.007 to about 0.07%, or from about 0.008 to about 0.07%, or from about 0.009 to about 0.07%, or from about 0.010 to about 0.07%, or from about 0.011 to about 0.07%, or from about 0.012 to about 0.07%, or from about 0.011 to about 0.07%, or from about 0.012 to about 0.07%, or from about 0.013 to about 0.07%, or from about 0.014 to about 0.07%, or from about 0.015 to about 0.07%, or from about 0.016 to about 0.07%, or from about 0.017 to about 0.07%, or from about 0.018 to about 0.07%, or from about 0.019 to about 0.07%, or from about 0.020 to about 0.07%, or from about 0.021 to about 0.07%, or from about 0.022 to about 0.07%, or from about 0.023 to about 0.07%, or from about 0.024 to about 0.07%, or from about 0.025 to about 0.07%, or from about 0.03 to about 0.07%, or from about 0.04 to about 0.07%, or from about 0.05 to about 0.07%, or from about 0.06 to about 0.07%, or from about 0.07 to about 0.07%, or from about 0.001 to about 0.06% w/w LAE, or from about 0.002 to about 0.06%, or from about 0.003 to about 0.06%, or from about 0.004 to about 0.06%, or from about 0.005 to about 0.06%, or from about 0.006 to about 0.06%, or from about 0.007 to about 0.06%, or from about 0.008 to about 0.06%, or from about 0.009 to about 0.06%, or from about 0.010 to about 0.06%, or from about 0.011 to about 0.06%, or from about 0.012 to about 0.06%, or from about 0.011 to about 0.06%, or from about 0.012 to about 0.06%, or from about 0.013 to about 0.06%, or from about 0.014 to about 0.06%, or from about 0.015 to about 0.06%, or from about 0.016 to about 0.06%, or from about 0.017 to about 0.06%, or from about 0.018 to about 0.06%, or from about 0.019 to about 0.06%, or from about 0.020 to about 0.06%, or from about 0.021 to about 0.06%, or from about 0.022 to about 0.06%, or from about 0.023 to about 0.06%, or from about 0.024 to about 0.06%, or from about 0.025 to about 0.06%, or from about 0.03 to about 0.06%, or from about 0.04 to about 0.06%, or from about 0.05 to about 0.06%, or from about 0.001 to about 0.05% w/w LAE, or from about 0.002 to about 0.05%, or from about 0.003 to about 0.05%, or from about 0.004 to about 0.05%, or from about 0.005 to about 0.05%, or from about 0.006 to about 0.05%, or from about 0.007 to about 0.05%, or from about 0.008 to about 0.05%, or from about 0.009 to about 0.05%, or from about 0.010 to about 0.05%, or from about 0.011 to about 0.05%, or from about 0.012 to about 0.05%, or from about 0.011 to about 0.05%, or from about 0.012 to about 0.05%, or from about 0.013 to about 0.05%, or from about 0.014 to about 0.05%, or from about 0.015 to about 0.05%, or from about 0.016 to about 0.05%, or from about 0.017 to about 0.05%, or from about 0.018 to about 0.05%, or from about 0.019 to about 0.05%, or from about 0.020 to about 0.05%, or from about 0.021 to about 0.05%, or from about 0.022 to about 0.05%, or from about 0.023 to about 0.05%, or from about 0.024 to about 0.05%, or from about 0.025 to about 0.05%, or from about 0.03 to about 0.05%, or from about 0.04 to about 0.05%, or from about 0.001 to about 0.04% w/w LAE, or from about 0.002 to about 0.04%, or from about 0.003 to about 0.04%, or from about 0.004 to about 0.04%, or from about 0.005 to about 0.04%, or from about 0.006 to about 0.04%, or from about 0.007 to about 0.04%, or from about 0.008 to about 0.04%, or from about 0.009 to about 0.04%, or from about 0.010 to about 0.04%, or from about 0.011 to about 0.04%, or from about 0.012 to about 0.04%, or from about 0.011 to about 0.04%, or from about 0.012 to about 0.04%, or from about 0.013 to about 0.04%, or from about 0.014 to about 0.04%, or from about 0.015 to about 0.04%, or from about 0.016 to about 0.04%, or from about 0.017 to about 0.04%, or from about 0.018 to about 0.04%, or from about 0.019 to about 0.04%, or from about 0.020 to about 0.04%, or from about 0.021 to about 0.04%, or from about 0.022 to about 0.04%, or from about 0.023 to about 0.04%, or from about 0.024 to about 0.04%, or from about 0.025 to about 0.04%, or from about 0.03 to about 0.04%, or from about 0.001 to about 0.03% w/w LAE, or from about 0.002 to about 0.03%, or from about 0.003 to about 0.03%, or from about 0.004 to about 0.03%, or from about 0.005 to about 0.03%, or from about 0.006 to about 0.03%, or from about 0.007 to about 0.03%, or from about 0.008 to about 0.03%, or from about 0.009 to about 0.03%, or from about 0.010 to about 0.03%, or from about 0.011 to about 0.03%, or from about 0.012 to about 0.03%, or from about 0.011 to about 0.03%, or from about 0.012 to about 0.03%, or from about 0.013 to about 0.03%, or from about 0.014 to about 0.03%, or from about 0.015 to about 0.03%, or from about 0.016 to about 0.03%, or from about 0.017 to about 0.03%, or from about 0.018 to about 0.03%, or from about 0.019 to about 0.03%, or from about 0.020 to about 0.03%, or from about 0.021 to about 0.03%, or from about 0.022 to about 0.03%, or from about 0.023 to about 0.03%, or from about 0.024 to about 0.03%, or from about 0.025 to about 0.03%, or from about 0.001 to about 0.025% w/w LAE, or from about 0.002 to about 0.025%, or from about 0.003 to about 0.025%, or from about 0.004 to about 0.025%, or from about 0.005 to about 0.025%, or from about 0.006 to about 0.025%, or from about 0.007 to about 0.025%, or from about 0.008 to about 0.025%, or from about 0.009 to about 0.025%, or from about 0.010 to about 0.025%, or from about 0.011 to about 0.025%, or from about 0.012 to about 0.025%, or from about 0.011 to about 0.025%, or from about 0.012 to about 0.025%, or from about 0.013 to about 0.025%, or from about 0.014 to about 0.025%, or from about 0.015 to about 0.025%, or from about 0.016 to about 0.025%, or from about 0.017 to about 0.025%, or from about 0.018 to about 0.025%, or from about 0.019 to about 0.025%, or from about 0.020 to about 0.025%, or from about 0.021 to about 0.025%, or from about 0.022 to about 0.025%, or from about 0.023 to about 0.025%, or from about 0.024 to about 0.025%, or from about 0.001 to about 0.023% w/w LAE, or from about 0.002 to about 0.023%, or from about 0.003 to about 0.023%, or from about 0.004 to about 0.023%, or from about 0.005 to about 0.023%, or from about 0.006 to about 0.023%, or from about 0.007 to about 0.023%, or from about 0.008 to about 0.023%, or from about 0.009 to about 0.023%, or from about 0.010 to about 0.023%, or from about 0.011 to about 0.023%, or from about 0.012 to about 0.023%, or from about 0.011 to about 0.023%, or from about 0.012 to about 0.023%, or from about 0.013 to about 0.023%, or from about 0.014 to about 0.023%, or from about 0.015 to about 0.023%, or from about 0.016 to about 0.023%, or from about 0.017 to about 0.023%, or from about 0.018 to about 0.023%, or from about 0.019 to about 0.023%, or from about 0.020 to about 0.023%, or from about 0.021 to about 0.023%, or from about 0.022 to about 0.023%, or from about 0.001 to about 0.022% w/w LAE, or from about 0.002 to about 0.022%, or from about 0.003 to about 0.022%, or from about 0.004 to about 0.022%, or from about 0.005 to about 0.022%, or from about 0.006 to about 0.022%, or from about 0.007 to about 0.022%, or from about 0.008 to about 0.022%, or from about 0.009 to about 0.022%, or from about 0.010 to about 0.022%, or from about 0.011 to about 0.022%, or from about 0.012 to about 0.022%, or from about 0.011 to about 0.022%, or from about 0.012 to about 0.022%, or from about 0.013 to about 0.022%, or from about 0.014 to about 0.022%, or from about 0.015 to about 0.022%, or from about 0.016 to about 0.022%, or from about 0.017 to about 0.022%, or from about 0.018 to about 0.022%, or from about 0.019 to about 0.022%, or from about 0.020 to about 0.022%, or from about 0.021 to about 0.022%, or from about 0.001 to about 0.021% w/w LAE, or from about 0.002 to about 0.021%, or from about 0.003 to about 0.021%, or from about 0.004 to about 0.021%, or from about 0.005 to about 0.021%, or from about 0.006 to about 0.021%, or from about 0.007 to about 0.021%, or from about 0.008 to about 0.021%, or from about 0.009 to about 0.021%, or from about 0.010 to about 0.021%, or from about 0.011 to about 0.021%, or from about 0.012 to about 0.021%, or from about 0.011 to about 0.021%, or from about 0.012 to about 0.021%, or from about 0.013 to about 0.021%, or from about 0.014 to about 0.021%, or from about 0.015 to about 0.021%, or from about 0.016 to about 0.021%, or from about 0.017 to about 0.021%, or from about 0.018 to about 0.021%, or from about 0.019 to about 0.021%, or from about 0.020 to about 0.021%, or from about 0.001 to about 0.020% w/w LAE, or from about 0.002 to about 0.020%, or from about 0.003 to about 0.020%, or from about 0.004 to about 0.020%, or from about 0.005 to about 0.020%, or from about 0.006 to about 0.020%, or from about 0.007 to about 0.020%, or from about 0.008 to about 0.020%, or from about 0.009 to about 0.020%, or from about 0.010 to about 0.020%, or from about 0.011 to about 0.020%, or from about 0.012 to about 0.020%, or from about 0.011 to about 0.020%, or from about 0.012 to about 0.020%, or from about 0.013 to about 0.020%, or from about 0.014 to about 0.020%, or from about 0.015 to about 0.020%, or from about 0.016 to about 0.020%, or from about 0.017 to about 0.020%, or from about 0.018 to about 0.020%, or from about 0.019 to about 0.020%, or from about 0.001 to about 0.019% w/w LAE, or from about 0.002 to about 0.019%, or from about 0.003 to about 0.019%, or from about 0.004 to about 0.019%, or from about 0.005 to about 0.019%, or from about 0.006 to about 0.019%, or from about 0.007 to about 0.019%, or from about 0.008 to about 0.019%, or from about 0.009 to about 0.019%, or from about 0.010 to about 0.019%, or from about 0.011 to about 0.019%, or from about 0.012 to about 0.019%, or from about 0.011 to about 0.019%, or from about 0.012 to about 0.019%, or from about 0.013 to about 0.019%, or from about 0.014 to about 0.019%, or from about 0.015 to about 0.019%, or from about 0.016 to about 0.019%, or from about 0.017 to about 0.019%, or from about 0.018 to about 0.019%, or from about 0.001 to about 0.018% w/w LAE, or from about 0.002 to about 0.018%, or from about 0.003 to about 0.018%, or from about 0.004 to about 0.018%, or from about 0.005 to about 0.018%, or from about 0.006 to about 0.018%, or from about 0.007 to about 0.018%, or from about 0.008 to about 0.018%, or from about 0.009 to about 0.018%, or from about 0.010 to about 0.018%, or from about 0.011 to about 0.018%, or from about 0.012 to about 0.018%, or from about 0.011 to about 0.018%, or from about 0.012 to about 0.018%, or from about 0.013 to about 0.018%, or from about 0.014 to about 0.018%, or from about 0.015 to about 0.018%, or from about 0.016 to about 0.018%, or from about 0.017 to about 0.018%, or from about 0.001 to about 0.017% w/w LAE, or from about 0.002 to about 0.017%, or from about 0.003 to about 0.017%, or from about 0.004 to about 0.017%, or from about 0.005 to about 0.017%, or from about 0.006 to about 0.017%, or from about 0.007 to about 0.017%, or from about 0.008 to about 0.017%, or from about 0.009 to about 0.017%, or from about 0.010 to about 0.017%, or from about 0.011 to about 0.017%, or from about 0.012 to about 0.017%, or from about 0.011 to about 0.017%, or from about 0.012 to about 0.017%, or from about 0.013 to about 0.017%, or from about 0.014 to about 0.017%, or from about 0.015 to about 0.017%, or from about 0.016 to about 0.017%, or from about 0.001 to about 0.016% w/w LAE, or from about 0.002 to about 0.016%, or from about 0.003 to about 0.016%, or from about 0.004 to about 0.016%, or from about 0.005 to about 0.016%, or from about 0.006 to about 0.016%, or from about 0.007 to about 0.016%, or from about 0.008 to about 0.016%, or from about 0.009 to about 0.016%, or from about 0.010 to about 0.016%, or from about 0.011 to about 0.016%, or from about 0.012 to about 0.016%, or from about 0.011 to about 0.016%, or from about 0.012 to about 0.016%, or from about 0.013 to about 0.016%, or from about 0.014 to about 0.016%, or from about 0.015 to about 0.016%, or from about 0.001 to about 0.015% w/w LAE, or from about 0.002 to about 0.015%, or from about 0.003 to about 0.015%, or from about 0.004 to about 0.015%, or from about 0.005 to about 0.015%, or from about 0.006 to about 0.015%, or from about 0.007 to about 0.015%, or from about 0.008 to about 0.015%, or from about 0.009 to about 0.015%, or from about 0.010 to about 0.015%, or from about 0.011 to about 0.015%, or from about 0.012 to about 0.015%, or from about 0.011 to about 0.015%, or from about 0.012 to about 0.015%, or from about 0.013 to about 0.015%, or from about 0.014 to about 0.015%, or from about 0.001 to about 0.014% w/w LAE, or from about 0.002 to about 0.014%, or from about 0.003 to about 0.014%, or from about 0.004 to about 0.014%, or from about 0.005 to about 0.014%, or from about 0.006 to about 0.014%, or from about 0.007 to about 0.014%, or from about 0.008 to about 0.014%, or from about 0.009 to about 0.014%, or from about 0.010 to about 0.014%, or from about 0.011 to about 0.014%, or from about 0.012 to about 0.014%, or from about 0.011 to about 0.014%, or from about 0.012 to about 0.014%, or from about 0.013 to about 0.014%, or from about 0.001 to about 0.013% w/w LAE, or from about 0.002 to about 0.013%, or from about 0.003 to about 0.013%, or from about 0.004 to about 0.013%, or from about 0.005 to about 0.013%, or from about 0.006 to about 0.013%, or from about 0.007 to about 0.013%, or from about 0.008 to about 0.013%, or from about 0.009 to about 0.013%, or from about 0.010 to about 0.013%, or from about 0.011 to about 0.013%, or from about 0.012 to about 0.013%, or from about 0.011 to about 0.013%, or from about 0.012 to about 0.013%, or from about 0.001 to about 0.012% w/w LAE, or from about 0.002 to about 0.012%, or from about 0.003 to about 0.012%, or from about 0.004 to about 0.012%, or from about 0.005 to about 0.012%, or from about 0.006 to about 0.012%, or from about 0.007 to about 0.012%, or from about 0.008 to about 0.012%, or from about 0.009 to about 0.012%, or from about 0.010 to about 0.012%, or from about 0.011 to about 0.012%, or from about 0.012 to about 0.012%, or from about 0.011 to about 0.012%, or from about 0.001 to about 0.011% w/w LAE, or from about 0.002 to about 0.011%, or from about 0.003 to about 0.011%, or from about 0.004 to about 0.011%, or from about 0.005 to about 0.011%, or from about 0.006 to about 0.011%, or from about 0.007 to about 0.011%, or from about 0.008 to about 0.011%, or from about 0.009 to about 0.011%, or from about 0.010 to about 0.011%, or from about 0.001 to about 0.01% w/w LAE, or from about 0.002 to about 0.01%, or from about 0.003 to about 0.01%, or from about 0.004 to about 0.01%, or from about 0.005 to about 0.01%, or from about 0.006 to about 0.01%, or from about 0.007 to about 0.01%, or from about 0.008 to about 0.01%, or from about 0.009 to about 0.01%, or from about 0.001 to about 0.009% w/w LAE, or from about 0.002 to about 0.009%, or from about 0.003 to about 0.009%, or from about 0.004 to about 0.009%, or from about 0.005 to about 0.009%, or from about 0.006 to about 0.009%, or from about 0.007 to about 0.009%, or from about 0.008 to about 0.009%, or from about 0.001 to about 0.008% w/w LAE, or from about 0.002 to about 0.008%, or from about 0.003 to about 0.008%, or from about 0.004 to about 0.008%, or from about 0.005 to about 0.008%, or from about 0.006 to about 0.008%, or from about 0.007 to about 0.008%, or from about 0.001 to about 0.007% w/w LAE, or from about 0.002 to about 0.007%, or from about 0.003 to about 0.007%, or from about 0.004 to about 0.007%, or from about 0.005 to about 0.007%, or from about 0.006 to about 0.007%, or from about 0.001 to about 0.006% w/w LAE, or from about 0.002 to about 0.006%, or from about 0.003 to about 0.006%, or from about 0.004 to about 0.006%, or from about 0.005 to about 0.006%, or from about 0.001 to about 0.005% w/w LAE, or from about 0.002 to about 0.005%, or from about 0.003 to about 0.005%, or from about 0.004 to about 0.005%, or from about 0.001 to about 0.004% w/w LAE, or from about 0.002 to about 0.004%, or from about 0.003 to about 0.004%, or from about 0.001 to about 0.003% w/w LAE, or from about 0.002 to about 0.003%, or from about 0.001 to about 0.002% w/w LAE. A more preferred concentration is in the range of 0.01 to 2.5% by weight and the most preferable concentration in the range of 0.01 to 0.1% by weight.

Hydrogen Peroxide

In parallel, the hydrogen peroxide is another molecule that acts as an antimicrobial, in particular in the food industry and in infection prevention treatment. Hydrogen peroxide presents a very broad spectrum of activity against for example viruses, vegetative bacteria, fungi, which includes a sporicidal activity, activity against hydrophilic viruses, and is effective against most germs involved in nosocomial infections. However, the antimicrobial action of hydrogen peroxide is of short duration and is limited to the superficial layer of the surface or tissue to which it is applied because it does not penetrate in said surface or tissue. Hydrogen peroxide alone is thus not suitable for preventing recontamination, especially on organic surfaces (e.g., human skin or fruits). Also, the surface of many fruits and vegetables can contain enough catalase or peroxidase enzymes to rapidly degrade hydrogen peroxide, especially when used at low concentrations. In contrast, high concentrations of hydrogen peroxide can cause skin irritation and, when used on food surfaces, cause oxidation and alters the structure or appearance of the food products (meats, fruits, vegetables . . . ). Another limitation to the use of hydrogen peroxide is that it is usually marketed to a maximum concentration of 35%. Also, when it is used alone at a concentration lower than 0.5% after a dilution, the spectrum antimicrobial activity is very limited. These two features greatly limits the possibilities of using hydrogen peroxides alone for use at high dilution rate like the one found in the food industry for some uses that require large volumes of antimicrobial solutions.

Furthermore, hydrogen peroxide is unstable and has a tendency to decompose, especially in the presence of metal ions. Also, it has the potential to damage soft metals, such as brass, copper, and aluminum, and carbon-tipped instruments. In this context a stabilizing agent may be added to stabilize and maintain the properties of hydrogen peroxide. Stabilizers of hydrogen peroxide include but are not limited to organophosphonates, colloidal stannate, silver ion, acetanilide, tin, phenol, organic and inorganic acid and their salt (eg. Sulfuric acid, sodium sulfate, sodium citrate, citric acid, sodium mono-polyphosphate, phosphoric acid or acid ascorbic).

The stabilizing agent may be from about 0.015 to about 0.5% w/w, or from about 0.03 to about 0.5% w/w, or from about 0.05 to about 0.5% w/w, or from about 0.1 to about 0.5% w/w, or from about 0.2 to about 0.5% w/w, or from about 0.3 to about 0.5% w/w, or from about 0.4 to about 0.5% w/w, or from about 0.015 to about 0.4% w/w, or from about 0.03 to about 0.4% w/w, or from about 0.05 to about 0.4% w/w, or from about 0.1 to about 0.4% w/w, or from about 0.2 to about 0.4% w/w, or from about 0.3 to about 0.4% w/w, or from about 0.015 to about 0.3% w/w, or from about 0.03 to about 0.3% w/w, or from about 0.05 to about 0.3% w/w, or from about 0.1 to about 0.3% w/w, or from about 0.2 to about 0.3% w/w, or from about 0.015 to about 0.2% w/w, or from about 0.03 to about 0.2% w/w, or from about 0.05 to about 0.2% w/w, or from about 0.1 to about 0.2% w/w, or from about 0.015 to about 0.1% w/w, or from about 0.03 to about 0.1% w/w, or from about 0.05 to about 0.1% w/w, or from about 0.015 to about 0.05% w/w, or from about 0.03 to about 0.05% w/w, or from about 0.015 to about 0.03% w/w, preferably from about 0.015 to about 0.03% w/w.

Hydrogen peroxide may be derived from oxidizing molecule in solid form such as solid peroxide salts, like sodium percarbonate, calcium peroxide, hydrogen peroxide-urea (i.e. carbamide peroxide). When solid forms of hydrogen peroxide are used, the final concentration of hydrogen peroxide to be used in the composition of the present invention is to be calculated relative to the amount (e.g. weight) of the hydrogen peroxide moiety present in the solid product, and thus excludes the other moiety.

Toxicity

Hydrogen peroxide may cause toxicity from all routes of exposure. Toxic effects in animals by all routes studied occurred only at levels several orders of magnitude greater than man's possible exposure from food sources (or other sources). At low concentration, residual $H_2O_2$ may be eliminated by endogenous catalase present on the surface of foods (fruits, vegetables, meat, etc.), but at high concentration or in case where low activity of catalase exists, the residual peroxide can cause undesirable oxidation change before degrading to oxygen and water.

The hydrogen peroxide containing compositions of the invention comprise from about 0.001% to about 35% w/w, or from about 0.01% to about 35%, or from about 0.1% to about 35%, or from about 1% to about 35%, or from about 1% to about 35%, or from about 2% to about 35%, or from about 3% to about 35%, or from about 4% to about 35%, or from about 5% to about 35%, or from about 6% to about 35%, or from about 7% to about 35%, or from about 8% to about 35%, or from about 9% to about 35%, or from about 10% to about 35%, or from about 11% to about 35%, or from about 12% to about 35%, or from about 13% to about 35%, or from about 14% to about 35%, or from about 15% to about 35%, or from about 16% to about 35%, or from about 17% to about 35%, or from about 18% to about 35%, or from about 19% to about 35%, or from about 20% to about 35%, or from about 21% to about 35%, or from about 22% to about 35%, or from about 23% to about 35%, or from about 24% to about 35%, or from about 25% to about 35%, or from about 26% to about 35%, or from about 27% to about 35%, or from about 28% to about 35%, or from about 29% to about 35%, or from about 30% to about 35%, or from about 31% to about 35%, or from about 32% to about 35%, or from about 33% to about 35%, or from about 34% to about 35%, or about 0.001% to about 34% w/w, or from about 0.01% to about 34%, or from about 0.1% to about 34%, or from about 1% to about 34%, or from about 1% to about 34%, or from about 2% to about 34%, or from about 3% to about 34%, or from about 4% to about 34%, or from about 5% to about 34%, or from about 6% to about 34%, or from about 7% to about 34%, or from about 8% to about 34%, or from about 9% to about 34%, or from about 10% to about 34%, or from about 11% to about 34%, or from about 12% to about 34%, or from about 13% to about 34%, or from about 14% to about 34%, or from about 15% to about 34%, or from about 16% to about 34%, or from about 17% to about 34%, or from about 18% to about 34%, or from about 19% to about 34%, or from about 20% to about 34%, or from about 21% to about 34%, or from about 22% to about 34%, or from about 23% to about 34%, or from about 24% to about 34%, or from about 25% to about 34%, or from about 26% to about 34%, or from about 27% to about 34%, or from about 28% to about 34%, or from about 29% to about 34%, or from about 30% to about 34%, or from about 31% to about 34%, or from about 32% to about 34%, or from about 33% to about 34%, or about 0.001% to about 33% w/w, or from about 0.01% to about 33%, or from about 0.1% to about 33%, or from about 1% to about 33%, or from about 1% to about 33%, or from about 2% to about 33%, or from about 3% to about 33%, or from about 4% to about 33%, or from about 5% to about 33%, or from about 6% to about 33%, or from about 7% to about 33%, or from about 8% to about 33%, or from about 9% to about 33%, or from about 10% to about 33%, or from about 11% to about 33%, or from about 12% to about 33%, or from about 13% to about 33%, or from about 14% to about 33%, or from about 15% to about 33%, or from about 16% to about 33%, or from about 17% to about 33%, or from about 18% to about 33%, or from about 19% to about 33%, or from about 20% to about 33%, or from about 21% to about 33%, or from about 22% to about 33%, or from about 23% to about 33%, or from about 24% to about 33%, or from about 25% to about 33%, or from about 26% to about 33%, or from about 27% to about 33%, or from about 28% to about 33%, or from about 29% to about 33%, or from about 30% to about 33%, or from about 31% to about 33%, or from about 32% to about 33%, or about 0.001% to about 32% w/w, or from about 0.01% to about 32%, or from about 0.1% to about 32%, or from about 1% to about 32%, or from about 1% to about 32%, or from about 2% to about 32%, or from about 3% to about 32%, or from about 4% to about 32%, or from about 5% to about 32%, or from about 6% to about 32%, or from about 7% to about 32%, or from about 8% to about 32%, or from about 9% to about 32%, or from about 10% to about 32%, or from about 11% to about 32%, or from about 12% to about 32%, or from about 13% to about 32%, or from about 14% to about 32%, or from about 15% to about 32%, or from about 16% to about 32%, or from about 17% to about 32%, or from about 18% to about 32%, or from about 19% to about 32%, or from about 20% to about 32%, or from about 21% to about 32%, or from about 22% to about 32%, or from about 23% to about 32%, or from about 24% to about 32%, or from about 25% to about 32%, or from about 26% to about 32%, or from about 27% to about 32%, or from about 28% to about 32%, or from about 29% to about 32%, or from about 30% to about 32%, or from about 31% to about 32%, or about 0.001% to about 31% w/w, or from about 0.01% to about 31%, or from about 0.1% to about 31%, or from about 1% to about 31%, or from about 1% to about 31%, or from about 2% to about 31%, or from about 3% to about 31%, or from about 4% to about 31%, or from about 5% to about 31%, or from about 6% to about 31%, or from about 7% to about 31%, or from about 8% to about 31%, or from about 9% to about 31%, or from about 10% to about 31%, or from about 11% to about 31%, or from about 12% to about 31%, or from about 13% to about 31%, or from about 14% to about 31%, or from about 15% to about 31%, or from about 16% to about 31%, or from about 17% to about 31%, or from about 18% to about 31%, or from about 19% to about 31%, or from about 20% to about 31%, or from about 21% to about 31%, or from about 22% to about 31%, or from about 23% to about 31%, or from about 24% to about 31%, or from about 25% to about 31%, or from about 26% to about 31%, or from about 27% to about 31%, or from about 28% to about 31%, or from about 29% to about 31%, or from about 30% to about 31%, or about 0.001% to about 30% w/w, or from about 0.01% to about 30%, or from about 0.1% to about 30%, or from about 1% to about 30%, or from about 1% to about 30%, or from about 2% to about 30%, or from about 3% to about 30%, or from about 4% to about 30%, or from about 5% to about 30%, or from about 6% to about 30%, or from about 7% to about 30%, or from about 8% to about 30%, or from about 9% to about 30%, or from about 10% to about 30%, or from about 11% to about 30%, or from about 12% to about 30%, or from about 13% to about 30%, or from about 14% to about 30%, or from about 15% to about 30%, or from about 16% to about 30%, or from about 17% to about 30%, or from about 18% to about 30%, or from about 19% to about 30%, or from about 20% to about 30%, or from about 21% to about 30%, or from about 22% to about 30%, or from about 23% to about 30%, or from about 24% to about 30%, or from about 25% to about 30%, or from about 26% to about 30%, or from about 27% to about 30%, or from about 28% to about 30%, or from about 29% to about 30%, or about 0.001% to about 29% w/w, or from about 0.01% to about 29%, or from about 0.1% to about 29%, or from about 1% to about 29%, or from about 1% to about 29%, or from about 2% to about 29%, or from about 3% to about 29%, or from about 4% to about 29%, or from about 5% to about 29%, or from about 6% to about 29%, or from about 7% to about 29%, or from about 8% to about 29%, or from about 9% to about 29%, or from about 10% to about 29%, or from about 11% to about 29%, or from about 12% to about 29%, or from about 13% to about 29%, or from about 14% to about 29%, or from about 15% to about 29%, or from about 16% to about 29%, or from about 17% to about 29%, or from about 18% to about 29%, or from about 19% to about 29%, or from about 20% to about 29%, or from about 21% to about 29%, or from about 22% to about 29%, or from about 23% to about 29%, or from about 24% to about 29%, or from about 25% to about 29%, or from about 26% to about 29%, or from about 27% to about 29%, or from about 28% to about 29%, or about 0.001% to about 28% w/w, or from about 0.01% to about 28%, or from about 0.1% to about 28%, or from about 1% to about 28%, or from about 1% to about 28%, or from about 2% to about 28%, or from about 3% to about 28%, or from about 4% to about 28%, or from about 5% to about 28%, or from about 6% to about 28%, or from about 7% to about 28%, or from about 8% to about 28%, or from about 9% to about 28%, or from about 10% to about 28%, or from about 11% to about 28%, or from about 12% to about 28%, or from about 13% to about 28%, or from about 14% to about 28%, or from about 15% to about 28%, or from about 16% to about 28%, or from about 17% to about 28%, or from about 18% to about 28%, or from about 19% to about 28%, or from about 20% to about 28%, or from about 21% to about 28%, or from about 22% to about 28%, or from about 23% to about 28%, or from about 24% to about 28%, or from about 25% to about 28%, or from about 26% to about 28%, or from about 27% to about 28%, or about 0.001% to about 27% w/w, or from about 0.01% to about 27%, or from about 0.1% to about 27%, or from about 1% to about 27%, or from about 1% to about 27%, or from about 2% to about 27%, or from about 3% to about 27%, or from about 4% to about 27%, or from about 5% to about 27%, or from about 6% to about 27%, or from about 7% to about 27%, or from about 8% to about 27%, or from about 9% to about 27%, or from about 10% to about 27%, or from about 11% to about 27%, or from about 12% to about 27%, or from about 13% to about 27%, or from about 14% to about 27%, or from about 15% to about 27%, or from about 16% to about 27%, or from about 17% to about 27%, or from about 18% to about 27%, or from about 19% to about 27%, or from about 20% to about 27%, or from about 21% to about 27%, or from about 22% to about 27%, or from about 23% to about 27%, or from about 24% to about 27%, or from about 25% to about 27%, or from about 26% to about 27%, or about 0.001% to about 26% w/w, or from about 0.01% to about 26%, or from about 0.1% to about 26%, or from about 1% to about 26%, or from about 1% to about 26%, or from about 2% to about 26%, or from about 3% to about 26%, or from about 4% to about 26%, or from about 5% to about 26%, or from about 6% to about 26%, or from about 7% to about 26%, or from about 8% to about 26%, or from about 9% to about 26%, or from about 10% to about 26%, or from about 11% to about 26%, or from about 12% to about 26%, or from about 13% to about 26%, or from about 14% to about 26%, or from about 15% to about 26%, or from about 16% to about 26%, or from about 17% to about 26%, or from about 18% to about 26%, or from about 19% to about 26%, or from about 20% to about 26%, or from about 21% to about 26%, or from about 22% to about 26%, or from about 23% to about 26%, or from about 24% to about 26%, or from about 25% to about 26%, or about 0.001% to about 25% w/w, or from about 0.01% to about 25%, or from about 0.1% to about 25%, or from about 1% to about 25%, or from about 1% to about 25%, or from about 2% to about 25%, or from about 3% to about 25%, or from about 4% to about 25%, or from about 5% to about 25%, or from about 6% to about 25%, or from about 7% to about 25%, or from about 8% to about 25%, or from about 9% to about 25%, or from about 10% to about 25%, or from about 11% to about 25%, or from about 12% to about 25%, or from about 13% to about 25%, or from about 14% to about 25%, or from about 15% to about 25%, or from about 16% to about 25%, or from about 17% to about 25%, or from about 18% to about 25%, or from about 19% to about 25%, or from about 20% to about 25%, or from about 21% to about 25%, or from about 22% to about 25%, or from about 23% to about 25%, or from about 24% to about 25%, or about 0.001% to about 24% w/w, or from about 0.01% to about 24%, or from about 0.1% to about 24%, or from about 1% to about 24%, or from about 1% to about 24%, or from about 2% to about 24%, or from about 3% to about 24%, or from about 4% to about 24%, or from about 5% to about 24%, or from about 6% to about 24%, or from about 7% to about 24%, or from about 8% to about 24%, or from about 9% to about 24%, or from about 10% to about 24%, or from about 11% to about 24%, or from about 12% to about 24%, or from about 13% to about 24%, or from about 14% to about 24%, or from about 15% to about 24%, or from about 16% to about 24%, or from about 17% to about 24%, or from about 18% to about 24%, or from about 19% to about 24%, or from about 20% to about 24%, or from about 21% to about 24%, or from about 22% to about 24%, or from about 23% to about 24%, or about 0.001% to about 23% w/w, or from about 0.01% to about 23%, or from about 0.1% to about 23%, or from about 1% to about 23%, or from about 1% to about 23%, or from about 2% to about 23%, or from about 3% to about 23%, or from about 4% to about 23%, or from about 5% to about 23%, or from about 6% to about 23%, or from about 7% to about 23%, or from about 8% to about 23%, or from about 9% to about 23%, or from about 10% to about 23%, or from about 11% to about 23%, or from about 12% to about 23%, or from about 13% to about 23%, or from about 14% to about 23%, or from about 15% to about 23%, or from about 16% to about 23%, or from about 17% to about 23%, or from about 18% to about 23%, or from about 19% to about 23%, or from about 20% to about 23%, or from about 21% to about 23%, or from about 22% to about 23%, or about 0.001% to about 22% w/w, or from about 0.01% to about 22%, or from about 0.1% to about 22%, or from about 1% to about 22%, or from about 1% to about 22%, or from about 2% to about 22%, or from about 3% to about 22%, or from about 4% to about 22%, or from about 5% to about 22%, or from about 6% to about 22%, or from about 7% to about 22%, or from about 8% to about 22%, or from about 9% to about 22%, or from about 10% to about 22%, or from about 11% to about 22%, or from about 12% to about 22%, or from about 13% to about 22%, or from about 14% to about 22%, or from about 15% to about 22%, or from about 16% to about 22%, or from about 17% to about 22%, or from about 18% to about 22%, or from about 19% to about 22%, or from about 20% to about 22%, or from about 21% to about 22%, or about 0.001% to about 21% w/w, or from about 0.01% to about 21%, or from about 0.1% to about 21%, or from about 1% to about 21%, or from about 1% to about 21%, or from about 2% to about 21%, or from about 3% to about 21%, or from about 4% to about 21%, or from about 5% to about 21%, or from about 6% to about 21%, or from about 7% to about 21%, or from about 8% to about 21%, or from about 9% to about 21%, or from about 10% to about 21%, or from about 11% to about 21%, or from about 12% to about 21%, or from about 13% to about 21%, or from about 14% to about 21%, or from about 15% to about 21%, or from about 16% to about 21%, or from about 17% to about 21%, or from about 18% to about 21%, or from about 19% to about 21%, or from about 20% to about 21%, or about 0.001% to about 20% w/w, or from about 0.01% to about 20%, or from about 0.1% to about 20%, or from about 1% to about 20%, or from about 1% to about 20%, or from about 2% to about 20%, or from about 3% to about 20%, or from about 4% to about 20%, or from about 5% to about 20%, or from about 6% to about 20%, or from about 7% to about 20%, or from about 8% to about 20%, or from about 9% to about 20%, or from about 10% to about 20%, or from about 11% to about 20%, or from about 12% to about 20%, or from about 13% to about 20%, or from about 14% to about 20%, or from about 15% to about 20%, or from about 16% to about 20%, or from about 17% to about 20%, or from about 18% to about 20%, or from about 19% to about 20%, or about 0.001% to about 19% w/w, or from about 0.01% to about 19%, or from about 0.1% to about 19%, or from about 1% to about 19%, or from about 1% to about 19%, or from about 2% to about 19%, or from about 3% to about 19%, or from about 4% to about 19%, or from about 5% to about 19%, or from about 6% to about 19%, or from about 7% to about 19%, or from about 8% to about 19%, or from about 9% to about 19%, or from about 10% to about 19%, or from about 11% to about 19%, or from about 12% to about 19%, or from about 13% to about 19%, or from about 14% to about 19%, or from about 15% to about 19%, or from about 16% to about 19%, or from about 17% to about 19%, or from about 18% to about 19%, or about 0.001% to about 18% w/w, or from about 0.01% to about 18%, or from about 0.1% to about 18%, or from about 1% to about 18%, or from about 1% to about 18%, or from about 2% to about 18%, or from about 3% to about 18%, or from about 4% to about 18%, or from about 5% to about 18%, or from about 6% to about 18%, or from about 7% to about 18%, or from about 8% to about 18%, or from about 9% to about 18%, or from about 10% to about 18%, or from about 11% to about 18%, or from about 12% to about 18%, or from about 13% to about 18%, or from about 14% to about 18%, or from about 15% to about 18%, or from about 16% to about 18%, or from about 17% to about 18%, or about 0.001% to about 17% w/w, or from about 0.01% to about 17%, or from about 0.1% to about 17%, or from about 1% to about 17%, or from about 1% to about 17%, or from about 2% to about 17%, or from about 3% to about 17%, or from about 4% to about 17%, or from about 5% to about 17%, or from about 6% to about 17%, or from about 7% to about 17%, or from about 8% to about 17%, or from about 9% to about 17%, or from about 10% to about 17%, or from about 11% to about 17%, or from about 12% to about 17%, or from about 13% to about 17%, or from about 14% to about 17%, or from about 15% to about 17%, or from about 16% to about 17%, or about 0.001% to about 16% w/w, or from about 0.01% to about 16%, or from about 0.1% to about 16%, or from about 1% to about 16%, or from about 1% to about 16%, or from about 2% to about 16%, or from about 3% to about 16%, or from about 4% to about 16%, or from about 5% to about 16%, or from about 6% to about 16%, or from about 7% to about 16%, or from about 8% to about 16%, or from about 9% to about 16%, or from about 10% to about 16%, or from about 11% to about 16%, or from about 12% to about 16%, or from about 13% to about 16%, or from about 14% to about 16%, or from about 15% to about 16%, or about 0.001% to about 15% w/w, or from about 0.01% to about 15%, or from about 0.1% to about 15%, or from about 1% to about 15%, or from about 1% to about 15%, or from about 2% to about 15%, or from about 3% to about 15%, or from about 4% to about 15%, or from about 5% to about 15%, or from about 6% to about 15%, or from about 7% to about 15%, or from about 8% to about 15%, or from about 9% to about 15%, or from about 10% to about 15%, or from about 11% to about 15%, or from about 12% to about 15%, or from about 13% to about 15%, or from about 14% to about 15%, or about 0.001% to about 14% w/w, or from about 0.01% to about 14%, or from about 0.1% to about 14%, or from about 1% to about 14%, or from about 1% to about 14%, or from about 2% to about 14%, or from about 3% to about 14%, or from about 4% to about 14%, or from about 5% to about 14%, or from about 6% to about 14%, or from about 7% to about 14%, or from about 8% to about 14%, or from about 9% to about 14%, or from about 10% to about 14%, or from about 11% to about 14%, or from about 12% to about 14%, or from about 13% to about 14%, or about 0.001% to about 13% w/w, or from about 0.01% to about 13%, or from about 0.1% to about 13%, or from about 1% to about 13%, or from about 1% to about 13%, or from about 2% to about 13%, or from about 3% to about 13%, or from about 4% to about 13%, or from about 5% to about 13%, or from about 6% to about 13%, or from about 7% to about 13%, or from about 8% to about 13%, or from about 9% to about 13%, or from about 10% to about 13%, or from about 11% to about 13%, or from about 12% to about 13%, or about 0.001% to about 12% w/w, or from about 0.01% to about 12%, or from about 0.1% to about 12%, or from about 1% to about 12%, or from about 1% to about 12%, or from about 2% to about 12%, or from about 3% to about 12%, or from about 4% to about 12%, or from about 5% to about 12%, or from about 6% to about 12%, or from about 7% to about 12%, or from about 8% to about 12%, or from about 9% to about 12%, or from about 10% to about 12%, or from about 11% to about 12%, or about 0.001% to about 11% w/w, or from about 0.01% to about 11%, or from about 0.1% to about 11%, or from about 1% to about 11%, or from about 1% to about 11%, or from about 2% to about 11%, or from about 3% to about 11%, or from about 4% to about 11%, or from about 5% to about 11%, or from about 6% to about 11%, or from about 7% to about 11%, or from about 8% to about 11%, or from about 9% to about 11%, or from about 10% to about 11%, or about 0.001% to about 10% w/w, or from about 0.01% to about 10%, or from about 0.1% to about 10%, or from about 1% to about 10%, or from about 1% to about 10%, or from about 2% to about 10%, or from about 3% to about 10%, or from about 4% to about 10%, or from about 5% to about 10%, or from about 6% to about 10%, or from about 7% to about 10%, or from about 8% to about 10%, or from about 9% to about 10%, or about 0.001% to about 9% w/w, or from about 0.01% to about 9%, or from about 0.1% to about 9%, or from about 1% to about 9%, or from about 1% to about 9%, or from about 2% to about 9%, or from about 3% to about 9%, or from about 4% to about 9%, or from about 5% to about 9%, or from about 6% to about 9%, or from about 7% to about 9%, or from about 8% to about 9%, or about 0.001% to about 8% w/w, or from about 0.01% to about 8%, or from about 0.1% to about 8%, or from about 1% to about 8%, or from about 1% to about 8%, or from about 2% to about 8%, or from about 3% to about 8%, or from about 4% to about 8%, or from about 5% to about 8%, or from about 6% to about 8%, or from about 7% to about 8%, or about 0.001% to about 7% w/w, or from about 0.01% to about 7%, or from about 0.1% to about 7%, or from about 1% to about 7%, or from about 1% to about 7%, or from about 2% to about 7%, or from about 3% to about 7%, or from about 4% to about 7%, or from about 5% to about 7%, or from about 6% to about 7%, or about 0.001% to about 6% w/w, or from about 0.01% to about 6%, or from about 0.1% to about 6%, or from about 1% to about 6%, or from about 1% to about 6%, or from about 2% to about 6%, or from about 3% to about 6%, or from about 4% to about 6%, or from about 5% to about 6%, or about 0.001% to about 5% w/w, or from about 0.01% to about 5%, or from about 0.1% to about 5%, or from about 1% to about 5%, or from about 1% to about 5%, or from about 2% to about 5%, or from about 3% to about 5%, or from about 4% to about 5%, or about 0.001% to about 4% w/w, or from about 0.01% to about 4%, or from about 0.1% to about 4%, or from about 1% to about 4%, or from about 1% to about 4%, or from about 2% to about 4%, or from about 3% to about 4%, or about 0.001% to about 3% w/w, or from about 0.01% to about 3%, or from about 0.1% to about 3%, or from about 1% to about 3%, or from about 1% to about 3%, or from about 2% to about 3%, or about 0.001% to about 2% w/w, or from about 0.01% to about 2%, or from about 0.1% to about 2%, or from about 1% to about 2%, or from about 1% to about 2%, or about 0.001% to about 1% w/w, or from about 0.01% to about 1%, or from about 0.1% to about 1%, or about 0.001% to about 0.1% w/w, or from about 0.01% to about 0.1%, or about 0.001% to about 0.01% w/w. Preferably from about 0.01 to 20% w/w, more preferably from about 0.05 to 10% by weight of the total composition.

Preferably the compositions also contain water, solvents, carriers or other suitable component in a quantity sufficient to make up 100% w/w.

Preferably, a weight ratio of LAE to Hydrogen peroxide is from 1:200 to 10:1, or from 1:100 to 5:1, preferably from 1:40 to 2:1, and most preferably from 1:5 to 1:1. In embodiments, the composition is used to bactericidal activity or prevent growth of bacteria, at a weight ratio of LAE to hydrogen peroxide from 1:100 to 5:1; or from 1:50 to 5:1; preferably from 1:20 to 4:1; and most preferably from 1:10 to 2:1. In embodiments, the composition is used for fungicidal activity or to prevent growth of fungi, at a weight ratio of the LAE to hydrogen peroxide from 1:50 to 5:1; or from 1:10 to 5:1; preferably from 1:5 to 5:1. In embodiments, the composition is used to prevent growth of bacterial spore, at a weight ratio of the LAE to hydrogen peroxide from 1:200 to 5:1; or from 1:100 to 2:1; or from 1:100 to 1:1; preferably from 1:10 to 1:1; and most preferably from 1:5 to 1:1.

Antimicrobial Activity

Hydrogen peroxide ($H_2O_2$) is an antiseptic (compared to a preservative) since it quickly acts to kill microorganisms and has no long-term or preserving effect. This short-lived action is due to hydrogen peroxide's rapid decomposition to oxygen and water upon contact with organic material. $H_2O_2$ demonstrates broad-spectrum efficacy against viruses, bacteria, yeasts, and bacterial spores. In general, greater activity is seen against gram-positive than gram-negative bacteria; however, the presence of catalase or other peroxidases in these organisms can increase tolerance in the presence of lower concentrations. Higher concentrations of $H_2O_2$ and longer contact times are required for sporicidal activity. Hydrogen peroxide has multiple targets within a cell, as well as in almost every biomolecule to produce an antimicrobial activity; these include peroxidation and disruption of membrane layers, oxidation of oxygen scavengers and thiol groups, enzyme inhibition, oxidation of nucleosides, impaired energy production, disruption of protein synthesis and, ultimately, cell death.

LAE is slightly more active against Gram-positive bacteria than against Gram-negative. Gram-negative organisms have a greater defense system and are less susceptible to the action of antibacterials since they possess an outer membrane surrounding the cell wall that restricts diffusion of hydrophobic compounds through its lipopolysaccharide covering. When used in foods, the cationic nature of LAE may reduce the antimicrobial effectiveness because of the potential for binding with anionic and hydrophobic food components.

According to an embodiment, the composition of the present invention may contain other additional functional ingredients from the group consisting of oxidizers, carriers, chelating and sequestering agents, hydrotropes, thickening, gelling agents, foaming inhibitor, film-forming agent, surfactants, coupling agents, acidulants, potentiators, corrosion inhibitor, anti-browning agent, antioxidant, flavouring aids, dye and mixtures thereof.

Sequestering Agent

Disinfectant concentrate formulations are typically prepared on site from mixtures of ingredients, and tap water is used for dilution. Tap water generally has a certain amount of hardness and metals ions. Since the presence of dissolved minerals (e.g. $Ca^{2+}$, $Mg^{2+}$, $Cu^{2+}$, $Fe^{2+}$) may adversely affect the performance and properties of the disinfectant formulation, a sequestering agent (polyvalent metal complexes or chelating agent) may be included in the formulation to chelate the dissolved minerals in the form of a water soluble complex. The chelating agent or sequestering agent can effectively complex and remove such ions from inappropriate interaction with active ingredients thus increasing sanitizing agent performance. Sequestering agents are well known in the art. Both organic and inorganic chelating agents may be used. Inorganic chelating agents include such compounds as sodium citrate, sodium mono or polyphosphate and other higher linear and cyclic polyphosphate species. Organic chelating agents include both polymeric and small molecule chelating agents. Polymeric chelating agents commonly comprise polyanionic compositions such as polyacrylic acid compounds and low molecular weight linear polyitaconic acid such as itaconic acid polymer, (e.g. Itaconix D2K®). Amino phosphates and phosphonates are suitable for use as chelating agents in the compositions of the invention and include ethylene diamine (tetramethylene phosphonates)(EDTA), ethylene glycol-bis(2-aminoethylether)-N,N,N',N'-tetraacetic acid (EGTA), nitrilotrismethylene phosphates, diethylenetriamine (pentamethylene phosphonates). These amino phosphonates commonly contain alkyl or alkaline groups with less than 8 carbon atoms. Organic acids and amino acids such as citric acid and glycine are also naturally occurring chelating agents and which are also suitable for use as chelating agents in the compositions of the invention.

The chelating agents that can be use in the present invention to improved any food additive chelating or sequestering agents such as disodium salts of ethylene diamine tetraacetic acid or the well-known phosphonates sold in the form of DEQUEST® materials, for example, 1-hydroxyethylidene-1,1-diphosphonic acid, etc. Preferred chelating agents for use in this invention include sequestering agent such as citric acid, sodium citrate, disodium pyrophosphate, potassium phosphate, sodium phosphate, phosphoric acid etc. Sequestering agents typically prevent the dissolved minerals from binding to the surfactant molecules or hydrogen peroxide. Moreover, sequestering agents may remove minerals from the surface to be disinfected.

Decomposition of hydrogen peroxide in aqueous solution by multivalent metal ions has long been a troublesome problem to those who make or handle solutions of hydrogen peroxide. Iron and copper are of special concern owing to their occurrence in common materials of reactor construction, water for dilution and catalyst supports. It is well known that copper and iron, even in the ppm range, will rapidly catalyze decomposition of hydrogen peroxide.

The extreme sensitivity of hydrogen peroxide solutions to metal-catalyzed decomposition becomes very significant because waters used to dilute hydrogen peroxide may, and often do, contain 1 mg iron, 0.2 mg copper, 0.1 mg manganese and 0.02 mg chromium per liter. These amounts are well above those causing rapid decomposition of hydrogen peroxide with economically unacceptable loss of materials and with associated hazards.

In solution, LAE is present in the form of micelle with a positive charge. The intensity of the charge depends in particular on the size of the particle and its organization. There appears to be a correlation between the increase in size and decrease in charge, which may have an impact on the antimicrobial activity. Furthermore, micelle size may also affect the solubility of the cationic surfactant LAE, which over time during the storage of the LAE molecule in solution which led to a reduction in the droplet charge and therefore to a decrease in the electrostatic repulsion between the droplets resulting in the formation of insoluble precipitates. In this context, it is important to stabilize the emulsion of LAE in aqueous base with a stabilizer like acid or sequestering agent, to ensure homogeneity of the solution (i.e. no precipitation) and preserve residual antimicrobial activity.

In another embodiment of the present invention, a buffering agent or an acidulant may be used. In some embodiments, the buffering agent helps the acidulant to maintain a pH between 2 and 7, for optimum antimicrobial activity of the disinfecting formulation, but also an acidic pH enables to stabilize in solution both the hydrogen peroxide and LAE. Thus, according to some embodiments, addition to stabilizing hydrogen peroxide, the addition of sequestering agent, buffering agent and/or acidulant may increase the stability and solubility of the solution formed with LAE.

The sequestering agent may be from about 0.0002 to about 10% w/w, or from about 0.002 to about 10% w/w, or from about 0.02 to about 10% w/w, or from about 0.2 to about 10% w/w, or from about 1 to about 10% w/w, or from about 5 to about 10% w/w, or from about 0.0002 to about 5% w/w, or from about 0.002 to about 5% w/w, or from about 0.02 to about 5% w/w, or from about 0.2 to about 5% w/w, or from about 1 to about 5% w/w, or from about 0.0002 to about 1% w/w, or from about 0.002 to about 1% w/w, or from about 0.02 to about 1% w/w, or from about 0.2 to about 1% w/w, or from about 0.0002 to about 0.2% w/w, or from about 0.002 to about 0.2% w/w, or from about 0.02 to about 0.2% w/w, or from about 0.0002 to about 0.02% w/w, or from about 0.002 to about 0.02% w/w, or from about 0.0002 to about 0.002% w/w, and preferably 0.0001 to about 0.5%.

Additional Antimicrobial Ingredient

The antimicrobial composition of the present invention may optionally include one or more additional antimicrobial ingredient for specific application on biopolymer or surface. The additional antimicrobials used in the present invention are preferably natural or considered GRAS or food additive raw materials. Some non-limiting examples include organic acid, chitosan, bacteriocin, essentials oils.

The inhibitory mechanism of organic acids occurs via diffusion of undissociated acids across the membrane barrier and subsequent dissociation in the cytoplasm which causes a number of physiological disruptions such as reduced intracellular pH. The combination of acetic acid with hydrogen peroxide produces the formation of peracetic acid, a powerful oxidant with antimicrobial properties. The peracetic acid can be use directly as additional antimicrobial ingredient.

Chitosan (CHIT; poly-$\beta$-(1$\rightarrow$4)-N-acetyl-D-glucosamine) is a natural biopolymer derived from deacetylation of chitin, which is a major structural component of exoskeleton of crustaceans. The exact antimicrobial mechanism of CHIT is still unclear but is thought to primarily involve cell membrane disruption, resulting from the association between the positively charged amino groups of chitosan and the negatively charged anions on the bacterial surface.

The bacteriocin are preferably GRAS or food additive. Non-limiting examples of bacteriocin that can be used in the context of the present invention include nisin (NIS), a bacteriocin produced naturally by *Lactococcus lactis* which is known to exhibit antimicrobial activity against a wide range of Gram positive bacteria. Antimicrobial action of NIS occurs through its binding to the lipid II in the membrane as the docking molecule and formation of transient pores in the cytoplasmic membrane, resulting in leakage of intracellular macromolecules and dissipation of the proton motive force.

Essential oils have the ability to disrupt the permeability barrier of cell membrane structures and the accompanying loss of chemiosmotic control is the most likely source of the lethal action at minimum inhibitory levels. The essential oils include oils derived from herbs, flowers, trees, and other plants. Such oils are typically present as tiny droplets between the plant's cells, and can be extracted by several methods known to those of skill in the art (e.g., steam distillation, enfleurage (i.e., extraction using fat(s)), maceration, solvent extraction, or mechanical pressing). Essential oils are typically named by the plant or vegetable in which the oil is found. For example, rose oil or peppermint oil is derived from rose or peppermint plants, respectively. Non-limiting examples of essential oils that can be used in the context of the present invention include oils of anise, lemon oil, orange oil, oregano oil, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, *eucalyptus* oil, tea tree oil, vervain oil, peppermint oil, gum benzoin, basil oil, fennel oil, fir oil, balsam oil, menthol, ocmea *origanum* oil, Hydastis carradensis oil, Berberidaceae daceae oil, Ratanhiae and *Curcuma longa* oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Also included in this class of essential oils are the key chemical components of the plant oils that have been found to provide the antimicrobial benefit (e.g. phenolic compounds like carvacrol, thymol, eugenol, menthol). The essential oils can be added in the composition by a technique of nanoemulsion.

Additional antimicrobial ingredients such as essential oil, and essential oil key ingredients may be present in the antimicrobial composition of the present invention from about 0.0001 to about 70% w/w, or from about 0.001 to about 70% w/w, or from about 0.01 to about 70% w/w, or from about 0.1 to about 70% w/w, or from about 1 to about 70% w/w, or from about 10 to about 70% w/w, or from about 20 to about 70% w/w, or from about 30 to about 70% w/w, or from about 40 to about 70% w/w, or from about 50 to about 70% w/w, or from about 60 to about 70% w/w, or from about 0.0001 to about 60% w/w, or from about 0.001 to about 60% w/w, or from about 0.01 to about 60% w/w, or from about 0.1 to about 60% w/w, or from about 1 to about 60% w/w, or from about 10 to about 60% w/w, or from about 20 to about 60% w/w, or from about 30 to about 60% w/w, or from about 40 to about 60% w/w, or from about 50 to about 60% w/w, or from about 0.0001 to about 50% w/w, or from about 0.001 to about 50% w/w, or from about 0.01 to about 50% w/w, or from about 0.1 to about 50% w/w, or from about 1 to about 50% w/w, or from about 10 to about 50% w/w, or from about 20 to about 50% w/w, or from about 30 to about 50% w/w, or from about 40 to about 50% w/w, or from about 0.0001 to about 40% w/w, or from about 0.001 to about 40% w/w, or from about 0.01 to about 40% w/w, or from about 0.1 to about 40% w/w, or from about 1 to about 40% w/w, or from about 10 to about 40% w/w, or from about 20 to about 40% w/w, or from about 30 to about 40% w/w, or from about 0.0001 to about 30% w/w, or from about 0.001 to about 30% w/w, or from about 0.01 to about 30% w/w, or from about 0.1 to about 30% w/w, or from about 1 to about 30% w/w, or from about 10 to about 30% w/w, or from about 20 to about 30% w/w, or from about 0.0001 to about 20% w/w, or from about 0.001 to about 20% w/w, or from about 0.01 to about 20% w/w, or from about 0.1 to about 20% w/w, or from about 1 to about 20% w/w, or from about 10 to about 20% w/w, or from about 0.0001 to about 10% w/w, or from about 0.001 to about 10% w/w, or from about 0.01 to about 10% w/w, or from about 0.1 to about 10% w/w, or from about 1 to about 10% w/w, or from about 0.0001 to about 1% w/w, or from about 0.001 to about 1% w/w, or from about 0.01 to about 1% w/w, or from about 0.1 to about 1% w/w, or from about 0.0001 to about 0.1% w/w, or from about 0.001 to about 0.1% w/w, or from about 0.01 to about 0.1% w/w, or from about 0.0001 to about 0.01% w/w, or from about 0.001 to about 0.01% w/w, or from about 0.0001 to about 0.001% w/w. Preferably, the concentration is from about 0.001-0.5% w/w.

Additional Ingredients

The antimicrobial composition may include additional functional ingredients that enhance the effectiveness of the composition or provide some other benefit. Examples of additional functional ingredients that may be included include long chain saturated or unsaturated fatty acids (e.g., $C_6$ to $C_{22}$), oxidizers, carriers, hydrotropes, thickening and/or gelling agents, foaming agents, foaming inhibitor, film-forming agents, surfactants, coupling agents, acidulants, potentiators, corrosion inhibitor, anti-browning, antioxidant, flavoring aids, fragrance, dye, and the like. Any additional functional ingredient is preferably a natural, GRAS or food grade ingredient.

Acidulant

According to an embodiment, the antimicrobial composition of the present invention may include one or more acidulants (or pH adjusting agent) for controlling the pH of the composition. The acidulants can be used in the present invention are preferably considered GRAS or food additive raw materials. Some non-limiting examples of suitable GRAS or food additive acidulants include lactic acid, phosphoric acid, sulfuric acid, adipic acid, tartaric acid, succinic acid, acetic acid, propionic acid, citric acid, malic acid, sodium acid sulfate, octenyl succinic acid, octanoic acid, glucolic acid, levulinic acid and mixtures thereof. The acidulant is preferably citric acid.

The exact amount of the acidulant in the composition will depend on the selection of the acidulant and the strength of the acidulant. The acidulant is preferably included in an amount to provide a desired pH. The pH of the ready-to-use composition is preferably from about 2.0 to about 7.0. A person of ordinary skill in the art will be able to determine the weight percentage of acidulant, in equilibrium, necessary to achieve the desired pH.

Acidulants may be present in the composition of the present invention at from about 0.0001 to about 1% w/w, or from about 0.001 to about 1% w/w, or from about 0.01 to about 1% w/w, or from about 0.1 to about 1% w/w, or from about 0.5 to about 1% w/w, or from about 0.0001 to about 0.5% w/w, or from about 0.001 to about 0.5% w/w, or from about 0.01 to about 0.5% w/w, or from about 0.1 to about 0.5% w/w, or from about 0.0001 to about 0.1% w/w, or from about 0.001 to about 0.1% w/w, or from about 0.01 to about 0.1% w/w, or from about 0.0001 to about 0.01% w/w, or from about 0.001 to about 0.01% w/w, or from about 0.0001 to about 0.001% w/w, and preferably from about 0.001 to about 0.5% w/w.

Buffers

According to another embodiment, the antimicrobial composition of the present invention may include one or more buffers. The buffer is preferably the conjugate base of the acidulant used in the composition. Further, the buffer is preferably considered to be a GRAS or food additive raw material. The buffer can be added directly to the composition in the form of the salt of the acidulant or formed by adding a neutralizing base to the acidulant. For example, if the buffer is created in the composition then a neutralizing base should be added to the acidulant to form the corresponding buffering salt. The neutralizing base is preferably considered natural, GRAS or food additive The buffer salts are preferably GRAS or food additive. Some non-limiting examples of suitable buffers include citric acid combined with sodium or potassium citrate, or phosphoric acid combined with monosodium phosphate, however, a person skilled in the art will be able to select the corresponding salt of the desired acidulant.

The buffer is preferably sodium or potassium citrate and sodium phosphate or disodium pyrophosphate.

The exact amount of the buffer in the composition will depend on the strength and amount of the acidulant and a person of ordinary skill in the art will be able to determine the exact weight percent of the buffer at equilibrium. The buffer may be present at about 0.001 to about 5% w/w, or about 0.01 to about 5% w/w, or about 0.1 to about 5% w/w, or about 1 to about 5% w/w, or about 0.001 to about 1% w/w, or about 0.01 to about 1% w/w, or about 0.1 to about 1% w/w, or about 0.001 to about 0.1% w/w, and preferably from about 0.001 to about 1% w/w.

Systemic Acquired Resistance Inducer

According to another embodiment, the antimicrobial composition of the present invention may include inducer of systemic acquired resistance (SAR), specifically when used as foliar treatment for plants. In the nature, the plants produce a response following an localized exposure to a pathogen and a inducer can simulate the activator of SAR response. The SAR inducer can be selected but not limited from the group consisting of silicate salt, acibenzolar-5-methyl, amino-n-butyric acid, aminobenzoic acid, riboflavin, salicylic acid.

The systemic acquired resistance inducer may be present at about 0.001 to about 10% w/w, or from about 0.01 to about 10% w/w, or from about 0.1 to about 10% w/w, or from about 1 to about 10% w/w, or from about 5 to about 10% w/w, or about 0.001 to about 5% w/w, or from about 0.01 to about 5% w/w, or from about 0.1 to about 5% w/w, or from about 1 to about 5% w/w, or about 0.001 to about 1% w/w, or from about 0.01 to about 1% w/w, or from about 0.1 to about 1% w/w, or about 0.001 to about 0.1% w/w, or from about 0.01 to about 0.1% w/w, or about 0.001 to about 0.01% w/w, or preferably from about 0.01 to about 0.1% w/w.

Long Chain Fatty Acids

According to another embodiment, the antimicrobial composition of the present invention may include a long chain fatty acid, and specifically a $C_6$ to $C_{22}$ fatty acid. Fatty acids are comprised of alkyl groups with 6 to 22 carbon atoms with a terminal carboxylic group (—COOH). Fatty acids may be saturated, with all of the alkyl chain carbon atoms connected by a single bond. Fatty acids can also be unsaturated, where there are one or more double bonds between the carbon atoms. Non-limiting examples of saturated fatty acids include hexanoic ($C_6$) acid, octanoic ($C_8$) acid, nonanoic ($C_9$) acid, decanoic ($C_{10}$) acid, lauric ($C_{12}$) acid, myristic ($C_{14}$) acid, palmitic ($C_{16}$) acid, stearic ($C_{18}$) acid, arachidic ($C_{20}$) acid, behenic ($C_{22}$) acid and the like. Non-limiting examples of unsaturated fatty acids include palmitoleic ($C_{16:1}$) acid, oleic ($C_{18:1}$) acid, linoleic ($C_{18:2}$) acid, linolenic ($C_{18:3}$) acid, arachidonic ($C_{20:1}$) acid and the like.

The long chain fatty acids may be present at about 0.0001 to about 5% w/w, or from about 0.001 to about 5% w/w, or from about 0.01 to about 5% w/w, or from about 0.1 to about 5% w/w, or from about 1 to about 5% w/w, or about 0.0001 to about 1% w/w, or from about 0.001 to about 1% w/w, or from about 0.01 to about 1% w/w, or from about 0.1 to about 1% w/w, or about 0.0001 to about 0.1% w/w, or from about 0.001 to about 0.1% w/w, or from about 0.01 to about 0.1% w/w, or about 0.0001 to about 0.01% w/w, or from about 0.001 to about 0.01% w/w, or about 0.0001 to about 0.001% w/w, and preferably from about 0.001 to about 0.5% w/w.

Oxidizers

According to another embodiment, the antimicrobial composition of the present invention may include another oxidizer. Some non-limiting examples of oxidizers include peroxygen compounds such as organic and inorganic peroxides, peracids, peresters, and mixtures thereof. Non-limiting examples of inorganic peroxides include: hydrogen peroxide salt, and other inorganic acids or salts of percarbonates, persulfates, and perborates. Non-limiting examples of organic peroxides include: benzoyl peroxide, tert-butyl benzoyl peroxide, and other alkyl and/or aryl peroxides. Non-limiting examples of peracids include: performic acid, peracetic acid, perlactic acid, perglycolic acid, chloroperbenzoic acid, perheptanoic acid, peroctanoic acid, perdecanoic acid, percitric acid, perbenzoic acid. Non-limiting examples of perester peracids include: monoester peracids derived from diacids or mono-ester diacids or diesters (e.g., such as adipic, succinic, glutaric, sebacic, or malonic acids/esters and mixtures thereof).

It is also possible to utilize oxidants capable of generating active oxidizing or oxygen species; including oxygen, ozone, chlorine dioxide, and mixtures thereof.

The oxidizer may be present at from about 0.001 to about 70% w/w, or from about 0.01 to about 70% w/w, or from about 0.1 to about 70% w/w, or from about 1 to about 70% w/w, or from about 10 to about 70% w/w, or from about 20 to about 70% w/w, or from about 30 to about 70% w/w, or from about 40 to about 70% w/w, or from about 50 to about 70% w/w, or from about 60 to about 70% w/w, or from about 0.001 to about 60% w/w, or from about 0.01 to about 60% w/w, or from about 0.1 to about 60% w/w, or from about 1 to about 60% w/w, or from about 10 to about 60% w/w, or from about 20 to about 60% w/w, or from about 30 to about 60% w/w, or from about 40 to about 60% w/w, or from about 50 to about 60% w/w, or from about 0.001 to about 50% w/w, or from about 0.01 to about 50% w/w, or from about 0.1 to about 50% w/w, or from about 1 to about 50% w/w, or from about 10 to about 50% w/w, or from about 20 to about 50% w/w, or from about 30 to about 50% w/w, or from about 40 to about 50% w/w, or from about 0.001 to about 40% w/w, or from about 0.01 to about 40% w/w, or from about 0.1 to about 40% w/w, or from about 1 to about 40% w/w, or from about 10 to about 40% w/w, or from about 20 to about 40% w/w, or from about 30 to about 40% w/w, or from about 0.001 to about 30% w/w, or from about 0.01 to about 30% w/w, or from about 0.1 to about 30% w/w, or from about 1 to about 30% w/w, or from about 10 to about 30% w/w, or from about 20 to about 30% w/w, or from about 0.001 to about 20% w/w, or from about 0.01 to about 20% w/w, or from about 0.1 to about 20% w/w, or from about 1 to about 20% w/w, or from about 10 to about 20% w/w, or from about 0.001 to about 10% w/w, or from about 0.01 to about 10% w/w, or from about 0.1 to about 10% w/w, or from about 1 to about 10% w/w, or from about 0.001 to about 1% w/w, or from about 0.01 to about 1% w/w, or from about 0.1 to about 1% w/w, or from about 0.001 to about 0.1% w/w, or from about 0.01 to about 0.1% w/w, or from about 0.001 to about 0.01% w/w, or from about 0.0001 to about 0.001% w/w. Preferably, the concentration is from about 0.001-0.5% w/w.

Carriers

According to another embodiment, the antimicrobial composition of the present invention may include a carrier or solvent. The carrier may be water or other solvent such as an alcohol or polyol. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g. propylene glycol, ethylene glycol, glycerine, and 1,2-propanediol). According to another embodiment, the carrier may be a solid carrier.

The carriers may be present at from about 0.0001 to about 99.99% w/w of the composition, essentially corresponding to the percentage of the amount remaining to attain 100% w/w.

Thickening Agents and Gelling Agents

According to another embodiment, the antimicrobial composition of the present invention may include a thickening agent and/or a gelling agent. Thickeners useful in the present invention are those which do not leave contaminating residue on the surface of application, i.e., constituents which are incompatible with food or other sensitive products in contact areas.

Generally, thickeners which may be used in the present invention include natural gums such as xanthan gum. Also useful in the present invention are cellulosic polymers, such as carboxymethyl cellulose. Generally, the concentration of thickener use in the present invention will be dictated by the desired viscosity within the final composition.

Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are salts of complex anionic polysaccharides. Synthetic natural-based thickeners having application are cellulosic derivatives wherein the free hydroxyl groups on the linear anhydro-glucose polymers have etherified or esterified to give a family of substances which dissolve in water and give viscous solutions. This group of materials includes the alkyl and hydroxyalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

The thickening agent and/or a gelling agent may be present at about 0.001 to about 20% w/w, or from about 0.01 to about 20% w/w, or from about 0.1 to about 20% w/w, or from about 1 to about 20% w/w, or from about 5 to about 20% w/w, or from about 10 to about 20% w/w, or from about 15 to about 20% w/w, or about 0.001 to about 15% w/w, or from about 0.01 to about 15% w/w, or from about 0.1 to about 15% w/w, or from about 1 to about 15% w/w, or from about 5 to about 15% w/w, or from about 10 to about 15% w/w, or about 0.001 to about 10% w/w, or from about 0.01 to about 10% w/w, or from about 0.1 to about 10% w/w, or from about 1 to about 10% w/w, or from about 5 to about 10% w/w, or about 0.001 to about 5% w/w, or from about 0.01 to about 5% w/w, or from about 0.1 to about 5% w/w, or from about 1 to about 5% w/w, or about 0.001 to about 1% w/w, or from about 0.01 to about 1% w/w, or from about 0.1 to about 1% w/w, or about 0.001 to about 0.1% w/w, or from about 0.01 to about 0.1% w/w, or about 0.001 to about 0.01% w/w, or preferably from about 0.01 to about 1% w/w.

Foaming Agents

According to another embodiment, the antimicrobial composition of the present invention may include foaming agent or foaming surfactant. Foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines like cocamidopropyl betaine (CAPB) and alkyl amides.

The foaming agent may be present at from about at about 0.001 to about 20% w/w, or from about 0.01 to about 20% w/w, or from about 0.1 to about 20% w/w, or from about 1 to about 20% w/w, or from about 5 to about 20% w/w, or from about 10 to about 20% w/w, or from about 15 to about 20% w/w, or about 0.001 to about 15% w/w, or from about 0.01 to about 15% w/w, or from about 0.1 to about 15% w/w, or from about 1 to about 15% w/w, or from about 5 to about 15% w/w, or from about 10 to about 15% w/w, or about 0.001 to about 10% w/w, or from about 0.01 to about 10% w/w, or from about 0.1 to about 10% w/w, or from about 1 to about 10% w/w, or from about 5 to about 10% w/w, or about 0.001 to about 5% w/w, or from about 0.01 to about 5% w/w, or from about 0.1 to about 5% w/w, or from about 1 to about 5% w/w, or about 0.001 to about 1% w/w, or from about 0.01 to about 1% w/w, or from about 0.1 to about 1% w/w, or about 0.001 to about 0.1% w/w, or from about 0.01 to about 0.1% w/w, or about 0.001 to about 0.01% w/w, or preferably from about 0.01 to about 1% w/w.

Film-Forming Agents

According to another embodiment, the antimicrobial composition of the present invention may also contain one or more rheology modifiers, to enhance viscosity, or thicken and cause the aqueous treatment to cling to the surface being treated. Clinging enables the composition to remain in contact with the transient and resident pathogenic bacteria for longer periods of time, thereby promoting microbiological efficacy and resisting waste because of excessive dripping. The rheology modifier may be a film former or may act cooperatively with a film forming agent to form a barrier that provides additional protection. Examples of useful rheology modifiers include, but are not limited to the following: colloidal aluminum silicate, colloidal clays, polyvinyl pyrrolidone, polyvinyl acetate, polyvinyl alcohol, polyalkylene oxides, polyacrylamides, chitosan or mixtures thereof.

Water soluble or water dispersible rheology modifiers that are useful can be classified as inorganic or organic. The organic thickeners can further be divided into natural synthetic polymers with the latter still further subdivided into synthetic natural-based synthetic petroleum-based.

Organic thickeners are generally compounds such as colloidal magnesium aluminum silicate (Veegum), colloidal clays (Bentonites), or silicas (Cab-O-Sils) which have been fumed to create particles with large surface size ratios.

The film forming agent may be present at from about 0.01 to about 50% w/w, or from about 0.1 to about 50% w/w, or from about 1 to about 50% w/w, or from about 10 to about 50% w/w, or from about 20 to about 50% w/w, or from about 30 to about 50% w/w, or from about 40 to about 50% w/w, or from about 0.01 to about 40% w/w, or from about 0.1 to about 40% w/w, or from about 1 to about 40% w/w, or from about 10 to about 40% w/w, or from about 20 to about 40% w/w, or from about 30 to about 40% w/w, or from about 0.01 to about 30% w/w, or from about 0.1 to about 30% w/w, or from about 1 to about 30% w/w, or from about 10 to about 30% w/w, or from about 20 to about 30% w/w, or from about 0.01 to about 20% w/w, or from about 0.1 to about 20% w/w, or from about 1 to about 20% w/w, or from about 10 to about 20% w/w, or from about 0.01 to about 10% w/w, or from about 0.1 to about 10% w/w, or from about 1 to about 10% w/w, or from about 0.01 to about 1% w/w, or from about 0.1 to about 1% w/w, or from about 0.01 to about 0.1% w/w, or preferably from about 0.1 to about 5%, or from about 1 to about 5% w/w.

Surfactants

According to another embodiment, the antimicrobial composition of the present invention a surfactant to help with detergency, surface wetting, and antimicrobial performance. Suitable surfactants include nonionic surfactants, anionic surfactants, cationic surfactants, amphoteric surfactants, amine oxides, and the like.

Additional suitable surfactants include nonionic surfactants of $C_6$-$C_{24}$ alcohol ethoxylates (preferably $C_6$-$C_{14}$ alcohol ethoxylates) having 1 to about 20 ethylene oxide groups (preferably about 9 to about 20 ethylene oxide groups); $C_6$-$C_{24}$ alkylphenol ethoxylates (preferably $C_8$-$C_{10}$ alkylphenol ethoxylates) having 1 to about 100 ethylene oxide groups (preferably about 12 to about 20 ethylene oxide groups); $C_6$-$C_{24}$ alkylpolyglycosides (preferably $C_6$-$C_{20}$ alkylpolyglycosides) having 1 to about 20 glycoside groups (preferably about 9 to about 20 glycoside groups); $C_6$-$C_{24}$ fatty acid ester ethoxylates, propoxylates or glycerides; and $C_4$-$C_{24}$ mono or dialkanolamides.

In addition, useful surfactants include those that perform a dual function. For example, surface active compounds such as mono, di and trialkyl phosphate esters may be added to the composition to aid in wetting, but also to suppress foam and provide some antimicrobial activity. Such phosphate esters would generally be produced from aliphatic linear alcohols, there being from 8 to 12 carbon atoms in the aliphatic portions of the alkyl phosphate esters. Nonionic surfactants, fatty acid salts, and silicone-based materials can be added to reduce foam formation herein. Such materials tend to enhance performance of the other components of the composition.

Highly preferred surfactants include food additive surfactants. Thus, the invention includes food grade, or naturally derived or food surface compatible, wetting and detersive agents, for example, linoleic acid, sorbitan esters, sugar esters, lecithins and ethoxylated lecithins, PEG alkylates, linear alkylbenzene sulfonates, stearyl citrate, alkyl naphthalene sulfonates, Pluronics, and various short-chain fatty acids.

The surfactant may be present at from about at about 0.001 to about 20% w/w, or from about 0.01 to about 20% w/w, or from about 0.1 to about 20% w/w, or from about 1 to about 20% w/w, or from about 5 to about 20% w/w, or from about 10 to about 20% w/w, or from about 15 to about 20% w/w, or about 0.001 to about 15% w/w, or from about 0.01 to about 15% w/w, or from about 0.1 to about 15% w/w, or from about 1 to about 15% w/w, or from about 5 to about 15% w/w, or from about 10 to about 15% w/w, or about 0.001 to about 10% w/w, or from about 0.01 to about 10% w/w, or from about 0.1 to about 10% w/w, or from about 1 to about 10% w/w, or from about 5 to about 10% w/w, or about 0.001 to about 5% w/w, or from about 0.01 to about 5% w/w, or from about 0.1 to about 5% w/w, or from about 1 to about 5% w/w, or about 0.001 to about 1% w/w, or from about 0.01 to about 1% w/w, or from about 0.1 to about 1% w/w, or about 0.001 to about 0.1% w/w, or from about 0.01 to about 0.1% w/w, or about 0.001 to about 0.01% w/w, or preferably from about 0.01 to about 1% w/w.

Potentiators

According to another embodiment, the antimicrobial composition of the present invention may optionally include a potentiator such as a terpenoid. Terpenoids are defined as materials with molecular structures containing carbon backbones made up of isoprene (2-methylbuta-1,3-diene) units. Isoprene contains five carbon atoms and therefore, the number of carbon atoms in any terpenoid is a multiple of five. It is believed that terpenoids assist in promoting the uptake of antimicrobial compounds and preservatives by cells of bacteria and fungi, thereby increasing the efficacy of the antimicrobial compound or preservative. Some non-limiting examples of terpenoids include α-terpinene, cineole, citral, citronellal, citronellol, farnesol, geraniol, limonene, linalool, methone, nerolidol, terpineol, camphene, menthone, myrcene, nerol, tetrahydrogeraniol, tetrahydrolinalool, apritone, and bisabolol.

The potentiator may be present at from about 0.001 to about 1% w/w, or from about 0.01 to about 1% w/w, or from about 0.1 to about 1% w/w, or from about 0.001 to about 0.1% w/w, or from about 0.01 to about 0.1% w/w, or from about 0.001 to about 0.01% w/w, preferably from about 0.01 to about 0.1% w/w.

Flavoring Aids, Fragrances, and Dyes

According to another embodiment, the antimicrobial composition of the present invention may include a flavoring aid for imparting a desired flavor to a food product or for masking an undesirable flavor. Some non-limiting examples of flavoring aids include marinades, tenderizers, and spices typically associated with food products.

According to another embodiment, the antimicrobial composition of the present invention may also include a fragrance including natural and synthetic fragrances. Some non-limiting examples of fragrances include aldehydes, ketones, esters, essential oils, and the like.

According to another embodiment, the antimicrobial composition of the present invention may include a dye.

These ingredients may be present at concentrations from about 0.0001 to about 2% w/w of the composition, preferably from about 0.0001 to about 0.01% w/w.

Corrosion Inhibitor

According to another embodiment, the antimicrobial composition of the present invention may include a corrosion inhibitor for decreases the corrosion rate of the material where the antimicrobial composition are pulverized. Non-limiting example of corrosion inhibitor include 1-hydroxyethylidene-1,1-diphosphonic acid.

The corrosion inhibitor may be present at concentrations from about 0.0002 to about 2% w/w of the composition, preferably from about 0.001 to about 0.5% w/w.

Antibrowning Agent and Antioxidant

According to another embodiment, the antimicrobial composition of the present invention may include a anti-browning agent for the prevention of browning in food, in particular in fresh cut and segmented fruit and vegetables. Under certain conditions an antioxidant agent may also be included in the composition to prevent degradation of hydrogen peroxide (eg. ascorbic acid or salt thereof). The anti-browning or antioxidants are food preferably food grade compound selected from non-limiting example include, ascorbic acid (Vitamin C) or derivatives or isomers thereof, for example, erythorbic acid. Other anti-browning agents which may include acidulants, such as natural acids found on fruits, for example, citric, malic, fumaric, lactic, succinic, pyruvic, oxalacetic, quinic or tartaric acids or acid polysaccharides, for example, alginic acid or pectinic acid or derivatives or isomers thereof; chelating agents, such as, ethylenediaminetetraacetic acid (EDTA) or sodium acid pyrophosphate; phenolase inhibitors, such as, 4-hexylresorcinol; complexing agents, such as, chitosan; inorganic salts, such as, calcium salts, for example, calcium carbonate, sulphate, chloride, phosphate or tartrate; an antioxidant enzyme; and mixtures thereof.

A preferred combination of anti-browning agents suitable for use in the composition of the invention is an antioxidant or reducing agent, such as, ascorbic or erythorbic acid; an acidulant to lower the pH, such as, citric acid or derivatives or isomers thereof; and calcium chloride.

The antibrowning agent and/or antioxidant may be present at concentrations from about 0.0002 to about 2% w/w of the composition, preferably from about 0.001 to about 0.5% w/w.

The antimicrobial compositions of the present invention may be formulated with different concentration of additional functional agents which are well known to those skilled in the art and which may facilitate the activity or use of the present invention. Here, for example, the table below shows the concentrations proposed in the use of ingredients useful, working or preferred.

| Constituent | Concentration (% w/w) | | |
|---|---|---|---|
| | Useful | Working | Preferred |
| Lauric arginate | 0.001-5 | — | 0.005-0.1 |
| Hydrogene peroxide | 0.001-35 | — | 0.05-10 |
| Stabilizing agent | — | 0.015-0.5 | 0.015-0.03 |
| Sequestering agent | — | 0.0002-10 | 0.0001-0.5 |
| Additional antimicrobial ingredients | — | 0.0001-70 | 0.001-0.5 |
| Acidulant | — | 0.0001-1 | 0.001-0.5 |
| Buffer | — | 0.001-5 | 0.001-1 |
| Fatty Acids | — | 0.001-5 | 0.001-0.5 |
| Oxidizers | — | 0.001-70 | 0.001-0.5 |
| Carriers | — | 0.0001-99.99 | 0.001-99.99 |
| Thickening Agents and Gelling Agents | — | 0.001-20 | 0.01-1 |

-continued

| Constituent | Concentration (% w/w) | | |
|---|---|---|---|
| | Useful | Working | Preferred |
| Foaming Agents | — | 0.001-20 | 0.01-1 |
| Film-Forming Agents | — | 0.01-50 | 0.1-5 |
| Surfactants | — | 0.001-20 | 0.01-1 |
| Potentiators | — | 0.001-1 | 0.001-0.1 |
| Systemic Acquired Resistance inducer | — | 0.001-10 | 0.01-0.1 |
| Fragrances | — | 0.0001-2 | 0.0001-0.01 |
| Corrosion inhibitor | — | 0.0002-2 | 0.001-0.5 |
| Antibrowning agent | — | 0.0002-2 | 0.001-0.5 |
| Antioxidant | — | 0.0002-2 | 0.001-0.5 |

Application of the Antimicrobial Composition

The antimicrobial compositions of the present invention may be formulated as a concentrate or a ready-to-use composition. A concentrate refers to the composition that is diluted to form the ready-to-use composition. The ready-to-use composition refers to the composition that is applied to a surface. A concentrate may be advantageous because it is less expensive to ship than a ready-to-use composition and it takes up less storage space. The concentrate may then be diluted to form a ready-to-use composition prior to application of the ready-to-use composition.

The antimicrobial composition may have a range of physical forms. For example, the antimicrobial composition may be a solid, liquid, structured or thickened liquid or gel, foam, pellet, prill, or a powder. Further, the antimicrobial composition may be a part of a dissolvable film such as polyvinylalcohol (PVA), PolyLacticAcid (PLA) or cellulose film, or the antimicrobial composition may be blown or extruded with a film, impregnated in a film, or coated on a film.

The antimicrobial composition may be part of the packaging that is applied to the food product. The antimicrobial composition of the present invention may be applied to the food product prior to, after, or substantially simultaneously with the packaging of the food product. Alternatively, the composition may be applied to the food product without packaging. The antimicrobial composition may be applied to the food product in several ways. In some embodiments, the antimicrobial composition may be applied directly to the food product in a number of ways including spraying, misting, rolling, vaporizing, and foaming the antimicrobial composition directly onto the food product and the like, and immersing the food product in the antimicrobial composition. The antimicrobial composition may be applied in an injection solution such as in an injection solution, or the antimicrobial composition may be applied as part of a marinade or tenderizer that is applied to the food product.

According to some embodiments, the antimicrobial composition of the present invention may be indirectly applied to the food product. The antimicrobial composition may be applied to the packaging prior to inserting the food product therein or prior to applying the packaging to the food product. The antimicrobial composition of the present invention then contacts the food product when the food product is packaged. As used herein, a "packaged food product" means a food product that has been placed in packaging but not yet sealed. The antimicrobial composition of the present invention may be applied to the packaging after the food product has been inserted into the packaging or after applying the packaging to the food product (e.g., the antimicrobial composition of the present invention may be squirted or otherwise introduced into the packaging after the food has been placed in the packaging but prior to sealing the packaging). The antimicrobial composition of the present invention may be applied to the food product substantially simultaneously with the packaging of the food product. Additionally, food packaging or food casing may be coated, treated, or impregnated with the antimicrobial composition of the present invention, and the antimicrobial composition is applied to the food product when the food product is placed inside the packaging or casing.

The present invention will be more readily understood by referring to the following examples which are given to illustrate the invention rather than to limit its scope.

Example 1

Synergistic Antimicrobial Effect of Hydrogen Peroxide and LAE

The antimicrobial effectiveness of the compositions of the present invention was tested. In this experiment, the test organism was $E.$ $coli$ and the final bacterial concentrations was $10^6$ to $10^7$ cfu/ml. Inoculum was contacted with either the combinations of LAE/$H_2O_2$ or individual, at different active concentration levels for a contact time of 30 seconds or more. The aliquots of this contaminated solution is used for determinate the minimal bactericidal concentration (MBC) for kill bacteria in the aliquots at 30 sec. contact time. Table 1 summarizes the efficacy of each biocide and their blends, and the Synergy index of each combination. In the same condition the minimal bactericidal time (MBT) was also evaluate with a combination of LAE:$H_2O_2$ (1:10) at different contact time. The table 2 summarizes the minimal bactericidal time for each biocide and a blend.

TABLE 1

Efficacy of each biocide and their blends
Biocide efficacy of $H_2O_2$, LAE, $H_2O_2$/
LAE combination, and synergy Index

| | MBC (active ppm) | | |
|---|---|---|---|
| Ratio LAE/$H_2O_2$ | LAE | $H_2O_2$ | Synergy Index* |
| 1:0 | >350 | | N/A |
| 1:40 | 50 | 2000 | <0.54 |
| 1:10 | 100 | 1000 | <0.49 |
| 1:2 | 200 | 500 | <0.67 |
| 5:1 | 300 | 50 | <0.87 |
| 1:0 | | 5000 | N/A |

*Synergy Index = Ca/CA + Cb/CB
Ca: Concentration of biocide A required to achieve a complete bacterial kill when used in combination with biocide B
CA: Concentration of biocide A required to achieve a complete bacterial kill when used alone
Cb: Concentration of biocide B required to achieve a complete bacterial kill when used in combination with biocide A
CB: Concentration of biocide B required to achieve a complete bacterial kill when used alone
Synergy Index: <1: synergy; =1: additivity; >1: antagonism

TABLE 2

Minimal bactericidal time for each biocide and a blend
Minimal bactericidal time (MBT) of $H_2O_2$,
LAE and LAE/$H_2O_2$ (1:10) combination

| active ppm | | |
|---|---|---|
| LAE | $H_2O_2$ | MBT |
| 100 | | 3 min. 30 sec. |
| 100 | 1000 | 30 sec. |
| | 1000 | >5 min. |

Example 2

Residual Effect of a Combination of LAE/$H_2O_2$ Compared with Peracetic Acid (PAA)

In the following example it is shown the residual effect of a combination of LAE/$H_2O_2$ compared with peracetic acid (PAA). The peracetic acid is often used in the food industry to sanitize food (fruit, vegetables, meat and poultry). The peracetic acid has a strong odor, is highly reactive and unstable when diluted and its use is limited to 80 ppm on food in the majority of countries worldwide regulation (e.g. US-FDA regulation 21CFR). For this example a solution of 200 ppm of lauric arginate with 1000 ppm of hydrogen peroxide is prepared and acidified to pH 2.5 using citric acid. The peracetic acid used is provided by Sigma-Aldrich.

Raw chicken pieces of the same size and weight are first soaked in an inoculating solution containing *E. coli* and incubated 30 minutes at 30° C. to allow the adhesion of bacteria on the surfaces of the sample. All samples are then soaked in a disinfectant solution (LAE/$H_2O_2$ or PAA) or a control (water) for a period of 30 seconds followed by a drying period drip for 2 minutes. Three replicates were completed per treatment. After the treatment, the samples were submerged in a neutralizing growth medium (D/E Neutralizing Broth) to analyze the populations of *E. coli* after the treatment or stored at room temperature in a sterile bags 24 hours before analyzed for populations of *E. coli*.

TABLE 3

Efficacy and inhibitory growth residual effect of LAE/H2O2 combination acidified with citric acid on *E. coli* on raw chicken piece

| Treatment Solution | Average Log10 cfu/sample 2 min. after treatment. | Log10 reduction vs control 2 min. after treatment. | Average Log10 cfu/sample 24 hours after treatment. |
|---|---|---|---|
| Untreated Control | 4.37 | N/A | 6.21 |
| LAE/$H_2O_2$ (200/1000 ppm) | 0.63 | 3.74 | 0.65 |
| PAA (80 ppm) | 0.56 | 3.81 | 2.51 |

The treatment of the raw chicken piece with the test sanitizer solution resulted in a >3 log reduction of *E. coli* after a contact time of 30 seconds. However, unexpectedly, after a incubation time of 24 hours at room temperature after the treatments only the LAE/$H_2O_2$ combination produced a significant inhibition of growth of bacteria on the piece of chicken.

Example 3

Sporicidal Activity of LAE/$H_2O_2$ Solution

The following example will demonstrate that a solution that combines the LAE/$H_2O_2$ sporicidal activity and then when diluted at low concentration can have a residual effect and act as an inhibitor of spore germination.

The determination of the sporicidal activity has been carried out on the base of the European standard EN 13704:2002 "Chemical disinfectant—Quantitative suspension test for the evaluation of sporicidal activity of chemical disinfectants used in food, industrial, domestic and institutional areas—Test method and requirements".

The sporicidal activity of a given product is defined by its capacity to reduce at least by 3 log (cfu/ml) the amount of *Bacillus subtilis* bacterial spores in suspension, in the conditions established in the method.

The test organism in the form of a test suspension was prepared containing endospores from *Bacillus subtilis* (ATCC#19659). The endospores were specifically prepared from a culture grown on Nutrient agar, to which additional sporulation enhancements were added. Plates were harvested with sterile water and endospores were purified by repeated centrifugations and resuspensions in water. The final wash was in 70% w/w ethanol for 30 minutes, to ensure the death of all vegetative bacteria.

To determining whether the tested sporicidal solutions may also act as inhibitor of spore germination when they are used at very low concentration (dilution 1/200 of concentred) the spore suspension was use to inoculate a sterile TSB media culture added with low concentration antimicrobial solution. The spore contaminated media culture was then incubated at 30° C. for 72 hours for detect the germination of the spore by the presence of a visually detectable growth. Three replicates were completed per treatment.

TABLE 4

Sporicidal activity and spore germination inhibition activity of hydrogen peroxide alone or in LAE combination on *B. subtilis* spore

| High concentration Treatment Solution | Average Log 10 cfu/ml reduction after 10 minutes contact time | Low concentration Treatment Solution (1:200 dilution of high concentration). | Spore germination inhibition activity |
|---|---|---|---|
| Control (water) | Not applicable | Control (water) | No inhibition |
| 10% $H_2O_2$ | >3 | 500 ppm $H_2O_2$ | No inhibition |
| 10% $H_2O_2$ in 10:1 ratio of $H_2O_2$:LAE combination | >3 | 50 ppm LAE, 500 ppm $H_2O_2$ | Inhibition |

The result present in the table 4 demonstrate that concentrations of 10% of hydrogen peroxide alone or in combination with LAE have a sporicidal activity but the spore germicidal activity in a low concentration treatment solutions (1:200 dilution of sporicide solution) is only observed when the hydrogen peroxide is combined with LAE. The sporicidal activity test with LAE alone shows no significant difference with the control in the tested experimental context (result not show).

Example 4

Concentred and Ready-to-Use Antimicrobial Composition

The antimicrobial effectiveness of the compositions of the present invention that include combination of lauric arginate (LAE) and hydrogen peroxide and that can be use with a food grade sequestering agent with buffering ability, an acidulant and an additional antimicrobial molecule was tested. An initial experiment was run to determine if the entire concentrate formulation (A-F) are stable and homogeneous when diluted 1:100 with distilled water, hard water or when stored at 4° C. (e.g. environmental conditions in some application). The formulation examples below (A-L) demonstrate the possibility of formulating the present invention as a concentrate or directly ready for use. These examples provide evidence of antimicrobial efficacy of the invention when used alone or in the presence of a sequestering agent, a buffer, a acidifant and a additional antimicrobial molecule.

TABLE 5 different composition of the present invention

| Examples | A | B | C | D | E | F | G | H | I | J | K | L |
|---|---|---|---|---|---|---|---|---|---|---|---|---|
| LAE | 2 | 2 | 2 | 2 | | 2 | 0.02 | 0.02 | 0.02 | 0.02 | | 0.02 |
| $H_2O_2$ | 10 | 10 | 10 | | 10 | | 0.1 | 0.1 | 0.1 | | 0.1 | |
| Citric acid | | 0.5 | 0.5 | 0.5 | 0.5 | | | 0.005 | 0.005 | 0.005 | 0.005 | |
| Sodium citrate | | 0.5 | 0.5 | 0.5 | 0.5 | 0.5 | | 0.005 | 0.005 | 0.005 | 0.005 | 0.005 |
| Carvacrol | | | 0.2 | 0.2 | 0.2 | | | | 0.002 | 0.002 | 0.002 | |
| Water | 88.0 | 87.0 | 86.8 | 96.8 | 88.8 | 97.5 | 99.88 | 99.87 | 99.87 | 99.97 | 99.89 | 99.98 |
| Total | 100 | 100 | 100 | 100 | 100 | 100 | 100 | 100 | 100 | 100 | 100 | 100 |

In each instance a comparative example was used in accordance with AOAC sanitizing testing procedures. The initial control concentration of *Listeria monocytogenes* was $8 \times 10^7$ cfu/ml. In each instance the efficacy of the compositions was measured after 60 seconds of contact time.

TABLE 6

Average Log10 cfu/ml reduction of compositions of the present invention described at table 5.

| Examples | Diluted with distilled water | Diluted with hard water (200 ppm $CaCO_3$) | Use at 4° C. and diluted with distilled water |
|---|---|---|---|
| G or A diluted 1:100 | >5 | 3.2 | >5 |
| H or B diluted 1:100 | >5 | >5 | >5 |
| I or C diluted 1:100 | >5 | >5 | >5 |
| J or D diluted 1:100 | 3.5 | 2.8 | 3.1 |
| K or E diluted 1:100 | 1.2 | 0.9 | 1.0 |
| L or F diluted 1:100 | 1.2 | 0.4 | Not soluble |

The combination of LAE and hydrogen peroxide achieves optimal results in bacterial load reduction. In hard water, the best results are obtained by the addition of sequestering agents. The use alone the LAE with a sequestering agent does not allow homogeneity of the solution when stored at 4° C.

Example 5

Bactericidal Activity

In the following example, the formulations of hand sanitizer M, N and O are evaluated for their antimicrobial activity. The test method is based on an AOAC method and the test organism was *E. coli*, which was contacted with the disinfecting solution inoculums for 60 seconds and then transferred in a D/E Neutralizing Broth medium. The transferred inoculums is evaluated as "no growth" (o) or "growth" (+) after a period of 48 hrs at 30° C. The results are shown in Table 7. As shown, the combination of lauric arginate and hydrogen peroxide enables a complete bactericidal activity, and surpassed the activity of lauric arginate or hydrogen peroxide alone at the same concentration.

TABLE 7

Formulations and bactericidal activity

| Examples | M | N | O |
|---|---|---|---|
| LAE | 0.01 | 0.01 | |
| $H_2O_2$ | 0.1 | | 0.1 |

TABLE 7-continued

Formulations and bactericidal activity

| Examples | M | N | O |
|---|---|---|---|
| Citric acid | 0.05 | 0.05 | 0.05 |
| Lactic acid | | | |
| Sodium citrate | 0.02 | 0.02 | 0.02 |
| Lauric acid | | | |
| Polylactic acid | | | |
| Glycerine | 1 | 1 | 1 |
| Chitosan | | | |
| Citral | 0.01 | 0.01 | 0.01 |
| Sodium Ascorbate | 0.1 | 0.1 | 0.1 |
| CAPB | 2 | 2 | 2 |
| glycoside | 2 | 2 | 2 |
| Water | 94.71 | 94.81 | 94.72 |
| Total | 100 | 100 | 100 |
| Bactericidal activity against *E. coli* - 60 seconds contact time. | o | + | + |

After 48 hrs incubation at 30° C.: o: no growth (bactericidal activity),
+: growth Example 6

Fungicidal Activity

Fungicidal activity as evaluated with different formulation of Antimicrobial Foliaire treatment for plants (M, N) and coating film with antimicrobial properties for hard surface (O, P, Q). The coating formulations (O, P, Q) are used to make a double-layer antimicrobial on a plastic film of polylactic acid (PLA). The inhibition of fungus spore germination was evaluated by agar plate test. Sabouraud dextrose agar plates are inoculated with spore of *Aspergillus niger* at the concentration of $2 \times 10^4$ spore/plate. The formulation M and N were sprayed once every two days to slightly cover all inoculated agar and immediately returned to the incubator. For the covered PLA film formulation O, P, Q, the film was deposited on the entire surface of the inoculated agar. Under optimal growing conditions, all the tested samples have been observed after 10 days of incubation to detect mycelium formation. Three replicates were completed per treatment.

The test results show that the composition of the invention when formulated as a foliar antimicrobial treatment of plants or as a coating film, they allow to inhibit the spores germination of *Aspergillus Niger*.

TABLE 8

Formulations and fungicidal activity

| Examples | M | N | O | P | Q |
|---|---|---|---|---|---|
| LAE | 0.005 | | 0.02 | 0.02 | |
| H₂O₂ | 0.05 | | 1.0 | 1.0 | |
| Citric acid | 0.01 | 0.01 | 0.5 | | 0.5 |
| Lactic acid | | | | 0.5 | |
| Salicylic acid | 0.01 | 0.01 | | | |
| Lauric acid | | | 0.01 | 0.01 | 0.01 |
| Chitosan | | | 4 | 4 | 4 |
| Sodium Ascorbate | 0.05 | 0.05 | 0.1 | 0.1 | 0.1 |
| Water | 99.87 | 99.93 | 94.37 | 93.37 | 95.39 |
| Total | 100 | 100 | 100 | 100 | 100 |
| Fungicidal activity against *Aspergilus niger* spore germination. | ○ | + | ○ | ○ | + |

After 10 days incubation at 30° C.: ○: no mycelium formation (fungicidal activity), +: mycelium formation While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. An antimicrobial composition comprising:
   a) Lauric arginate ethyl ester;
   b) hydrogen peroxide; and
   c) a sequestering agent.

2. The antimicrobial composition of claim 1, further comprising a carrier.

3. The composition of claim 1, wherein concentration said of lauric arginate ethyl ester is of at least about 5 ppm or is from about 0.001% to about 5% w/w or is from about 0.01% to about 2.5% w/w or is from about 0.01% to about 0.1% w/w.

4. The composition of claim 1, wherein concentration of said hydrogen peroxide is of at least about 5 ppm or is from about 0.001% to about 35% w/w, or is from about 0.01% to about 20% w/w, or is from about 0.05% to about 15% w/w.

5. The composition of claim 1, wherein said lauric arginate ethyl ester and said hydrogen peroxide are in a weight ratio of about 1:200 to about 10:1, or of about 1:100 to about 5:1, or of about 1:40 to about 2:1, or of about 1:5 to about 1:1.

6. The composition of claim 5, wherein said lauric arginate ethyl ester and said hydrogen peroxide are in a weight ratio of about 1:40, or 1:10, or 1:2, or 5:1.

7. The composition of claim 1, wherein concentration of said sequestering agent is from about 0.0001 to about 2% w/w of the composition.

8. The composition of claim 1, further comprising a stabilizing agent.

9. The composition of claim 8, wherein concentration of said stabilizing agent is from about 0.015% to about 0.5% w/w of the composition.

10. The composition of claim 1, further comprising an additional ingredient selected from the group consisting of an oxidizer, a hydrotrope, a thickening agent, a gelling agent, a foaming agent, a foaming inhibitor, a film-forming agent, a surfactant, a coupling agent, a acidulant, a potentiator, a buffering agent, a corrosion inhibitor, an antibrowning agent, an antioxidant, a systemic acquired resistance inducer, a long chain fatty acid, a flavouring agent, a fragrance, a dye, and mixtures thereof.

11. The composition of claim 10, wherein concentration of said acidulant is from about 0.0001% to about 1% w/w of the composition.

12. The composition of claim 10, wherein concentration of said buffering agent is from about 0.001% to about 5% w/w of the composition.

13. The composition of claim 10, wherein concentration of said long chain fatty acids is from about 0.0001% to about 5% w/w of the composition.

14. The composition of claim 10, wherein said oxidizer is selected from benzoyl peroxide, tert-butyl benzoyl peroxide, performic acid, peracetic acid, perlactic acid, perglycolic acid, chloroperbenzoic acid, perheptanoic acid, peroctanoic acid, perdecanoic acid, percitric acid, perbenzoic acid, adipic acid, succinic acid, glutaric acid, sebacic acid, or malonic acid, oxygen, ozone, chlorine dioxide, and combinations thereof.

15. The composition of claim 10, wherein concentration of said oxidizer is from about 0.001 to about 70% w/w of said composition.

16. The composition of claim 2, wherein said carrier is selected from water, a solvent, a combination thereof, or a solid carrier.

17. The composition of claim 2, wherein said carrier is present in a quantity sufficient to reach 100% w/w.

18. The composition of claim 10, wherein concentration of said thickening agent and/or a gelling agent is about 0.001 to about 20% w/w of said composition.

19. The composition of claim 10, wherein concentration of said film-forming agent is from about 0.01 to about 50% w/w of said composition.

20. The composition of claim 10, wherein concentration of said surfactant is from about 0.001 to about 20% w/w of said composition.

21. The composition of claim 10, wherein concentration of said potentiator is from about 0.001 to about 1% w/w.

22. The composition of claim 10, wherein concentration of said systemic acquired resistance inducer is from about 0.001 to about 10% w/w of said composition.

23. The composition of claim 1, wherein a pH of said composition is about 2.0 to about 7.0.

24. A method of disinfecting a surface comprising contacting said surface with a composition according to claim 1.

25. The method of claim 24, wherein said surface comprises the surface of fruit or vegetables or the surface of a meat product, an animal carcass, a live poultry, a live animal, human skin, or a plant or the surface of a food processing equipment, a hard surface, a porous surface, a medical equipment, a surface in a health care facility.

26. The composition of claim 10, wherein concentration of said foaming agent is from about 0.001 to about 20% w/w of said composition.

27. The composition of claim 10, wherein said antibrowning agent or antioxidant is selected from ascorbic acid or derivatives or isomers thereof, citric acid, malic acid, fumaric acid, lactic acid, succinic acid, pyruvic acid, oxalacetic acid, quinic acid, tartaric acid, alginic acid, pectinic acid, ethylenediaminetetraacetic acid (EDTA), sodium acid pyrophosphate, 4-hexylresorcinol, chitosan, calcium carbonate, calcium sulphate, calcium chloride, calcium phosphate, calcium tartrate, an antioxidant enzyme, and mixtures thereof.

* * * * *